US011901063B2

(12) United States Patent
Scherrer et al.

(10) Patent No.: US 11,901,063 B2
(45) Date of Patent: *Feb. 13, 2024

(54) NAVIGABLE PRESENTATION OF A VARIETY OF SOLUTIONS FOR THERAPY PLANS

(71) Applicant: FRAUNHOFER-GESELLSCHAFT ZUR FOERDERUNG DER ANGEWANDTEN FORSCHUNG E.V., Munich (DE)

(72) Inventors: Alexander Scherrer, Kaiserslautern (DE); Karl-Heinz Kuefer, Weilerbach (DE); Philipp Suess, Budenheim (DE); Michael Bortz, Kaiserslautern (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 305 days.

This patent is subject to a terminal disclaimer.

(21) Appl. No.: 17/359,936

(22) Filed: Jun. 28, 2021

(65) Prior Publication Data

US 2021/0327558 A1 Oct. 21, 2021

Related U.S. Application Data

(63) Continuation of application No. 15/818,258, filed on Nov. 20, 2017, now Pat. No. 11,049,602, which is a (Continued)

(30) Foreign Application Priority Data

Dec. 23, 2011 (DE) .......................... 102011057038.1

(51) Int. Cl.
*G16H 20/10* (2018.01)
*G16H 20/40* (2018.01)
(Continued)

(52) U.S. Cl.
CPC ......... *G16H 20/40* (2018.01); *G06F 3/04842* (2013.01); *G06F 3/04845* (2013.01);
(Continued)

(58) Field of Classification Search
CPC ........ G16H 20/10; G16H 40/63; G16H 10/60; G16H 70/20; G16H 20/40; G06F 3/04842;
(Continued)

(56) References Cited

U.S. PATENT DOCUMENTS 6,038,283 A 3/2000 Carol et al.
6,393,096 B1 5/2002 Carol et al.
(Continued)

FOREIGN PATENT DOCUMENTS

DE 10151987 C2 11/2003
DE 10318204 B4 11/2004
(Continued)

OTHER PUBLICATIONS

Philips sense and simplicity; Raise your expectations: Philips Pinnacle 9.2; philips.com/radiationoncology; Koninklijke Philips Electronics N.V.; pp. 1-4; 2012.
(Continued)

*Primary Examiner* — Peter H Choi
*Assistant Examiner* — Chad A Newton
(74) *Attorney, Agent, or Firm* — TROUTMAN PEPPER HAMILTON SANDERS LLP; Christopher J. Forstner; Brandon M. Reed

(57) ABSTRACT

The present invention includes a method for representing a plurality of pre-calculated solutions in radiation therapy that are stored in a database and displayed in a manner controllable by a user. Arrays of DVH curves provide the user with essential information on the 'quality of a plan'. A DVH diagram is displayed as a main diagram, wherein only one
(Continued)

of the solutions is visually represented at a time. By selecting a first starting point on a selected DVH curve as the main diagram, a first straight axis extending through the first starting point is placed. A first region, located around the first starting point and on the first straight axis, is highlighted as a first control region for controllable visualization of the plurality of currently non-displayed solutions stored in the database, the DVH curves of which correspond to the selected DVH curve and intersect the first straight axis.

5 Claims, 25 Drawing Sheets

Related U.S. Application Data continuation of application No. 14/359,771, filed as application No. PCT/IB2012/057559 on Dec. 20, 2012, now Pat. No. 9,824,187.

(51) Int. Cl.
| | |
|---|---|
| G16H 40/63 | (2018.01) |
| G16H 10/60 | (2018.01) |
| G16H 70/20 | (2018.01) |
| G06F 3/04842 | (2022.01) |
| G06F 3/04845 | (2022.01) |
| G06T 11/20 | (2006.01) |
| G06T 11/60 | (2006.01) |

(52) U.S. Cl.
CPC ............ *G06T 11/206* (2013.01); *G06T 11/60* (2013.01); *G16H 10/60* (2018.01); *G16H 20/10* (2018.01); *G16H 40/63* (2018.01); *G16H 70/20* (2018.01); *G06T 2200/24* (2013.01); *G06T 2210/32* (2013.01); *G06T 2210/41* (2013.01)

(58) Field of Classification Search
CPC .. G06F 3/04845; G06F 19/321; G06F 19/325; G06T 11/206; G06T 11/60; G06T 2200/24; G06T 2210/32; G06T 2210/41
See application file for complete search history.

(56) References Cited

U.S. PATENT DOCUMENTS

| | | | |
|---|---|---|---|
| 6,792,074 B2 | 9/2004 | Erbel et al. | |
| 7,391,026 B2 | 6/2008 | Trinkaus et al. | |
| 7,831,289 B2 | 11/2010 | Riker et al. | |
| 2005/0079511 A1* | 4/2005 | Mandema ............... | G16H 50/50 702/19 |
| 2005/0111621 A1* | 5/2005 | Riker ..................... | G16H 20/40 378/65 |
| 2005/0116172 A1* | 6/2005 | Trinkaus ................. | G16H 70/20 250/363.02 |
| 2006/0274885 A1 | 12/2006 | Wang et al. | |
| 2010/0054411 A1 | 3/2010 | Nord et al. | |
| 2013/0304503 A1 | 11/2013 | Kuefer et al. | |

FOREIGN PATENT DOCUMENTS

| | | |
|---|---|---|
| DE | 69737508 T2 | 11/2007 |
| DE | 102010062079 A1 | 8/2012 |
| EP | 0952874 B1 | 12/2004 |
| EP | 0952875 B1 | 3/2007 |
| EP | 2260902 A1 | 12/2010 |
| WO | 98/17349 A1 | 4/1998 |
| WO | 2004093971 A2 | 11/2004 |
| WO | 2005035061 A2 | 4/2005 |
| WO | 2011153639 A2 | 12/2011 |

OTHER PUBLICATIONS

ELEKTA; XiO Comprehensive RTP system; Create treatment plans with precision; elekta.com; ELEKTA AB (publ), Stockholm, Sweden; pp. 1-8; Doc. LPCXIO090709 v3.0; 2011.
ELEKTA; Monaco State-of-the-art planning; Redefine treatment precision and conformance; elekta.com; ELEKTA AB (publ), Stockholm, Sweden; Art. LPCMON090520 v3.0; 2011.
ELEKTA CMS Software; XiO Great Performances; cmsrtp.com; ELEKTA AB (publ), Stockholm, Sweden; Art.LPCXIO090709 v1.0; 2009.
ELEKTA; Focal Distributed Planning System; Freedom from boundaries; elekta.com; ELEKTA AB (publ), Stockholm, Sweden; Doc. LPCFCL090713 v3.0; 2011.
Nucletron an ELEKTA Company; Oncentra External Beam; Integrated solution for external beam treatment planning; Open, fast and accurate treatment planning; nucletron.com, elekta.com; ELEKTA AB (publ), Stockholm, Sweden; pp. 1-8; Art. 888.00347 MKT [00]; 2013.
Nucletron an ELEKTA Company; Oncentra Prostate for Nucletron HDR Real-time Prostate Solution; nucletron.com, elekta.com; ELEKTA AB (publ), Stockholm, Sweden; pp. 1-4; Art. 888.00245US MKT [02]; 2012.
Corvus Inverse Treatment Planning; Best nomos healthcare for everyone; One Best Drive, Pittsburgh, PA, US; 2008.
David Craft and Michael Monz; Simultaneous Navigation of multiple Pareto Surfaces, with an Application to multi-criteria IMRT planning with multiple beam angle configurations; Dec. 8, 2009.
Philipp Suess; A primal-dual barrier algorithm for the IMRT planning problem—An application of optimization-driven adaptive discretization; pp. 1-137; Jun. 2008.
Christian Thieke et al.; A new concept for interactive radiotherapy planning with multicriteria optimization: First clinical evaluation; Radiotherapy and Oncology, Elsevier, Ireland, vol. 85, No. 2; XP_22363696A; pp. 292-298; Nov. 1, 2007.
Thomas Bortfeld; Optimized Planning Using Physical Objectives and Constraints; Seminars in Radiation Oncology, Saunders, Philadelphia, PA, US, vol. 9, No. 1; XP_5454727A; pp. 20-34; Jan. 1, 1999.
Michael Monz et al.; Pareto Navigation—algorithmic foundation of interactive multi-criteria IMRT planning; Physics in Medicine and Biology, Institute of Physics Publishing, Bristol GB, vol. 53, No. 4; XP_20127372A; pp. 985-998; Feb. 21, 2008.
Siemens AG; Better Approach for Presenting Dose Volume Histogram (DVH); IP.com Journal, IP.com Inc., West Henrietta; NY, US; XP_13126132A; Sep. 24, 2008.
Michael Goitein and Thomas Miller; Planning proton therapy of the eye; Medical Physics, vol. 10, No. 3; pp. 275 to 283; May/Jun. 1983.
William U. Shipley et al.; Proton Radiation as Boost Therapy for Localized Prostatic Carcinoma; Journal of the American Medical Association, vol. 241, No. 18; pp. 1912-1915; May 4, 1979.
RaySearch Laboratories; Multi Criteria Optimization in Raystation; raysearchlabs.com; Raysearch Laboratories AB, Stockholm, Sweden, presently assumed to be prior to the priority date, the properties of the pdf file suggest Aug. 2012.
Michael Monz; Pareto Navigation—interactive multiobjective optimisation and its application in radiotherapy planning; pp. 1-157; Jun. 2006.
Serna et al.; Trade-off bounds for the Pareto surface approximation in multi-criteria IMRT planning; Physics in Medicine and Biology, Institute of Physics Publishing, Bristol GB, vol. 54; pp. 6299-6311; Oct. 7, 2009.
Filka Yaneva; Modeling and Navigation of Tumor Conformality in IMRT Planning; Fraunhofer ITWM Kaiserslautern; pp. 1-83; Apr. 1, 2009.
Filka Yaneva et al.; An alternative view on global radiotherapy optimization problems; Reports of the Fraunhofer ITWM No. 165; pp. 1-20; Jul. 6, 2009.
www.rtog.org/ClinicalTrials/ProtocolTable.aspx publication date unknown, regularly updated site.
ICRU Report 78—Prescribing, Recording, and Reporting Proton-Beam Therapy, Oxford University Press, Journal of the ICRU, vol.

(56) References Cited

OTHER PUBLICATIONS

7, No. 2, 2007, cover attached, please visit www.icru.org/home/reports/prescribing-recording-and-reporting-proton-beam-therapy-icru-report-78.

ICRU Report 83—Prescribing, Recording and Reporting Photon-Beam Intensity-Modulated Radiation Therapy (IMRT), Oxford University Press, Journal of the ICRU, vol. 10, No. 1, 2010, cover attached, please visit www.icru.org/testing/reports/prescribing-recording-and-reporting-intensity-modulated-photon-beam-therapy-imrt-icru-report-83.

https://www.youtube.com/watch?feature=player_embedded&v=-VTrxQIQyjl RaySearch, Personalized Care at RISO with Multi-Criteria Optimization in RayStation, Jan. 30, 2015.

https://www.youtube.com/watch?feature=player_embedded&v=JqQiE4vdfA0 RaySearch, Introduction to Multi-Criteria Optimization in RayStation, Feb. 6, 2015.

Bentzen, Constine, Deasy, Eisbruch, Jackson, Marks, Ten Haken, Yorke, Quantitative Analyses of normal tissue effects in the clinic (QUANTEC): An introduction to the scientific issues, International Journal of Radiation Oncology Biology Physics, vol. 76, 2010, pp. 3 to 9.

Shipley, WU, Tepper, JE, Prout, GR, Verhey, LJ, Mendiondo, OA, Goitein, M, Koehler, AM, Suit, HD, Proton radiation as boost therapy for localized prostatic Carcinoma, Journal of the American Medical Association, vol. 241, 1979, pp. 1912 to 1915.

Rasmus Bokrantz, Multicriteria optimization for managing tradeoffs in radiation therapy treatment planning, Doctoral Thesis, Stockholm, Sweden, May 2013.

Wayne Newhauser, Review of ICRU 78, Prescribing, Recording and Reporting Proton-Beam Therapy, Published by International Commission on Radiation Units and Measurements, ISBN 1473-6691, pp. 210 ff, 2007.

Avraham (Avi) Eisbruch et al., Phase III Study of Conformal and Intensity Modulated Irradiation for Oropharyngeal Cancer, Study, Jul. 7, 2004, includes Revision 1-4 (Broadcast Jul. 22, 2004).

Chad A. Newton; Office Action; U.S. Appl. No. 14/359,771; dated Feb. 16, 2017; United States Patent and Trademark Office; Alexandria, Virginia.

Chad A. Newton; Notice of Allowance and Fees Due; U.S. Appl. No. 14/359,771; dated Jul. 17, 2017; United States Patent and Trademark Office; Alexandria, Virginia.

Ralf Abbing; International Search Report and Written Opinion; International Patent Application No. PCT/IB2012/057559; dated Apr. 16, 2013; European Patent Office; Rijswijk, Netherlands.

Ralf Abbing; International Preliminary Report on Patentability-Chapter II; International Application No. PCT/IB2012/057559; dated May 9, 2014; European Patent Office; Rijswijk, Netherlands.

* cited by examiner

FIG. 15c
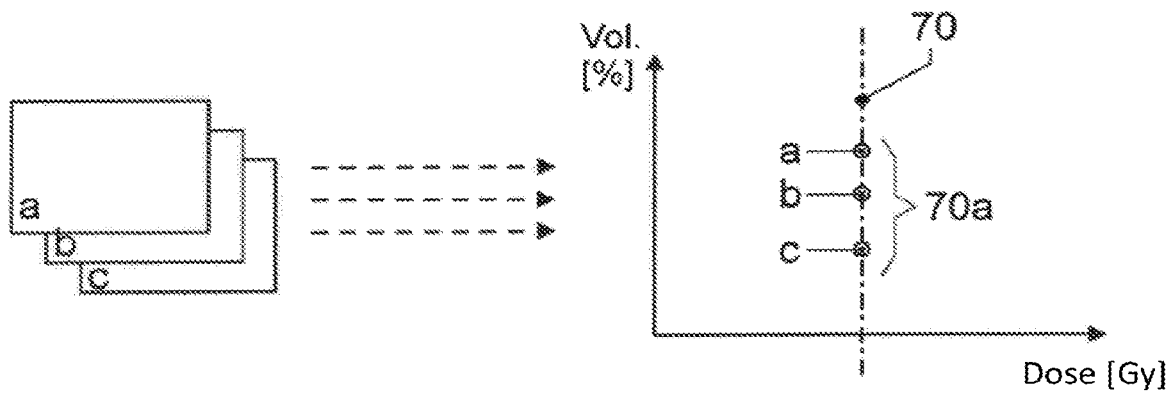
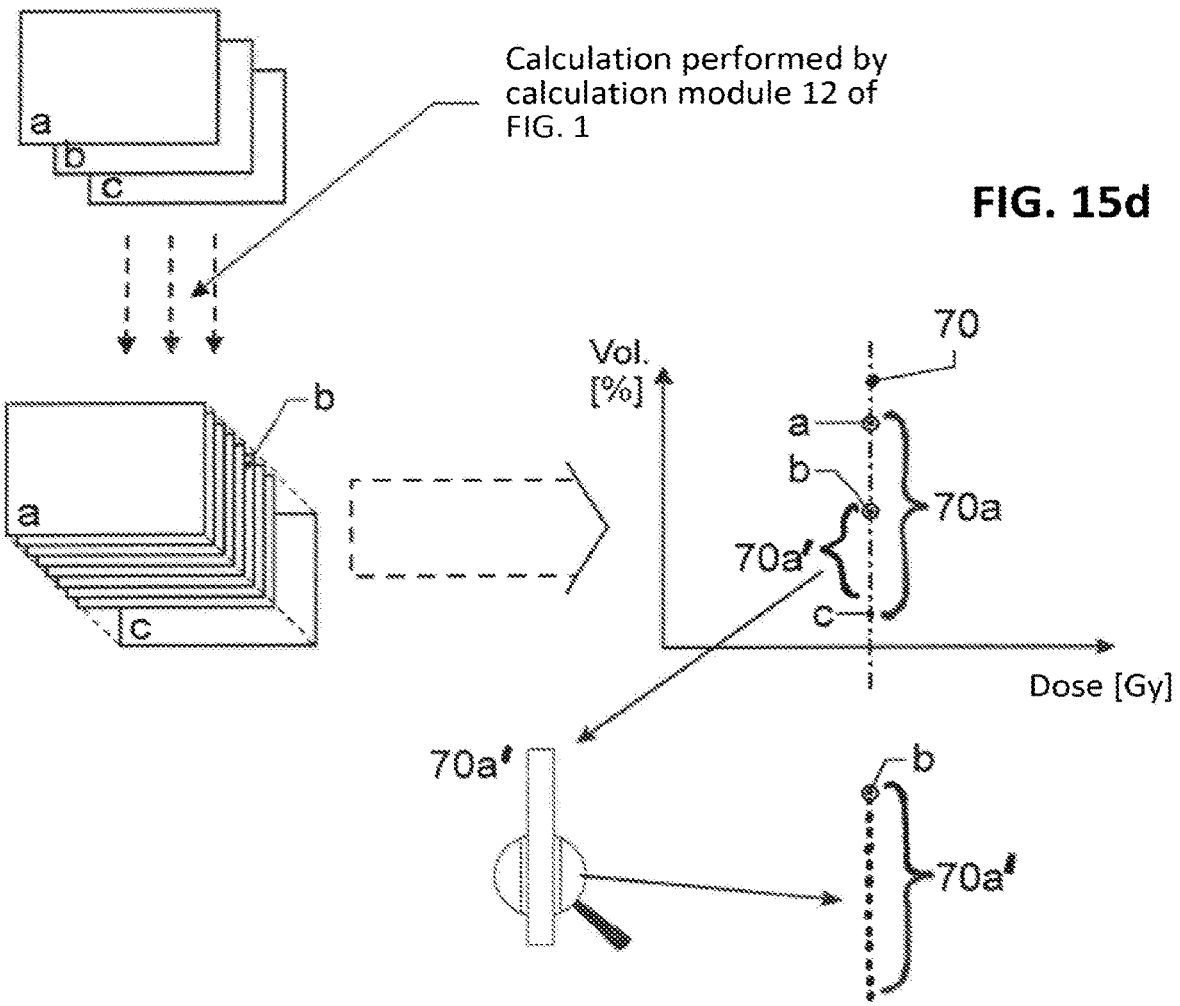
FIG. 15d

NAVIGABLE PRESENTATION OF A VARIETY OF SOLUTIONS FOR THERAPY PLANS

CROSS REFERENCE TO RELATED APPLICATIONS

This application is a continuation of, and claims priority under 35 U.S.C. § 120 to, U.S. patent application Ser. No. 15/818,258, filed Nov. 20, 2017, which is a continuation of U.S. patent application Ser. No. 14/359,771, filed Oct. 1, 2014, now U.S. Pat. No. 9,824,187, which is a 371 of International Application No. PCT/IB2012/057559, filed Dec. 20, 2012, which claims priority to DE 102011057038.1, filed Dec. 23, 2011, the entire contents of each of which are fully incorporated herein by reference.

FIELD OF THE INVENTION

The invention relates to a specific kind of graphic representation of a variety of solutions in clinical, intensity-modulated radiation therapy (IMRT). The latter is characterized by a novel kind of multi-criteria optimization (MCO). As a result, a higher quality of plans and reduced expenditure of time is achieved.

A planning tool is claimed as well.

BACKGROUND OF THE INVENTION

Medically speaking, a plan means that a patient receives a therapy. The plan is defined by a variety of technical parameters which can be determined by settings on the irradiation device. These involve times, intensities, angular positions, longitudinal positions of a treatment table (depending on the therapy device), type of radiation and a variety of other technical parameters to be determined for a patient.

It is referred to—as is customary in the medical language—as a "plan". Technically speaking, the plan is a variety of technical parameters determining this plan and specified to the technical device. The therapy or irradiation resulting therefrom is the inevitable consequence of the previous setting of the applicable parameters. All these parameters have technical characteristics, they thus represent a technical factor in the device, which is realistically implemented by the device when an appropriate programming and appropriate functionality of the technology is provided.

U.S. Pat. No. 7,391,026 B2 (Fraunhofer) illustrates such a control method or planning tool combining MCO with IMRT and defining a variety of technical parameters for a plan to be determined which can be entered into the device illustrated therein, cf. FIG. 1 thereof, which is incorporated herein, wherein the device illustrated therein, which is also used herein, is not represented and explained again. The description thereof is incorporated by reference.

SUMMARY OF THE INVENTION

There is a need in the prior art to provide a user with an advanced, refined variant, somewhat returning from the full abstraction as disclosed by Fraunhofer for navigation. The user or planner is in need to be put in a position to still be able to think in his accustomed and conventional tracks, wherein an important user orientation in these user accustomed, conventional tracks is provided by arrays (or groups) of DVH (dose volume histogram) curves. They provide the user/planner with essential information on the quality of a 'plan'. In the mentioned Fraunhofer document, this array of DVH curves had an illustrating function only, it was a result of a 'plan' determined in a different fully abstract way, see FIG. 6, bottom left, of Fraunhofer.

The need is satisfied according to the claimed invention by the fact that the method of representation operates with the arrays (or group) of DVH curves and represents them visually, putting a user in a position to develop plans, or interactively identify respective solutions from the stored variety of solutions (corresponding to the plans).

The method represents a variety of pre-calculated solutions in an optically visible manner. This is implemented on a display device which can comprise a conventional monitor as well as a manually operable tablet PC. The variety of pre-calculated solutions for possible plans, which are stored in a database in a pre-calculated state, is displayed on the display device such that the user is enabled to work with this variety of solutions. It is to be noted that it is not the user's way of working or his expert knowledge which is used here in accordance with the claims, rather they are configured such that the solution (to the above-mentioned need) is complete when a plurality of pre-calculated solutions can be displayed on the display device in such a manner that the user is at all enabled to control this variety or the display thereof so that his desired aim is achieved in a simple manner.

Control of the display device is implemented on the basis of a basic representation. The basic representation is a DVH diagram being displayed as a main diagram. A variety of pre-calculated solutions can be represented on this DVH diagram, however, only one of these solutions is visually represented at a time. Such a solution comprises a group of defined volumes, each being associated with a visually represented curve.

The normal approach to a DVH curve diagram involves plotting percent by volume over dose. A plot-point on curves indicates the amount of percent by volume that maintains a minimum amount of radiation dose. A selected point having, for example, a radiation dose of 60 Gy (Gray) and having a corresponding value of 28% on the percent-by-volume axis indicates that: A dose value of at least 60 Gy is maintained in 28% of the viewed volume (by the plan and the therapy). It results therefrom that a curve representing a risk is ideally very steep in the initial section (about 0 Gy to 10 Gy), i.e. a radiation dose as low as possible and a volume as large as possible. The inverse ideal case for a target (the affected tumor volume) is a curve remaining at 100% for a very long time and dropping very steeply at a very late stage only in order to irradiate a percentage of the volume as high as possible with a dose value as high as possible.

This desired qualitative result is rarely achieved, in most cases the curves are between those two extremes. Risks are irradiated to a higher degree than per se desired, and targets are irradiated to a lesser degree than actually desired. The object is to determine solutions preferably "optimized" in a multi-criteria manner such that the risks are irradiated to a just tolerable extent and the targets receive a sufficient dose to control the tumor.

The representation of a solution in the DVH diagram is based on the viewed volumes. Among these volumes are tumor area(s), healthy organs and anatomic entities or also relevant and thus separately defined tissue regions (volumes). Even though only one solution is displayed at a time, a variety of other solutions are available in the database—underlying the display—which have already been pre-calculated and optimized in a multi-criteria manner. They are also represented by way of "control of representation (visualization)", as explained in the following.

Apart from the main diagram, at least one auxiliary diagram can be provided representing another display format with respect to the solution currently represented in the DVH diagram as the main diagram.

The auxiliary diagram(s) can, for example, be diagrams indicating isodose lines (isodoses), i.e. three sectionals views in directions perpendicular to each other, wherein the volumes corresponding to the DVH curves in the main diagram are additionally represented by suitable outlines or contours. Each curve of the main diagram is thus associated with a corresponding volume in the three sectional views perpendicular to each other and with the corresponding isodose lines. This is an example of another kind of visualization (or: representation) outside of the representation of the DVH diagram. Other possibilities include replacing the three sectional views by a three-dimensional representation so that only one auxiliary diagram is present. This three-dimensional representation can also be rotated on the light screen in order to be represented from various directions of view.

In addition, a planning tool for interactively selecting suitable solutions in the sense of therapy plans is suggested, which are each composed of a number of technical control parameters for operating such a technical device at a later stage which, however, is not the subject matter of the claims.

A starting point is selected on one of the DVH curves. This staring point lies on the selected DVH curve, a plurality of which is represented in the main diagram. This representation, which is referred to as "array of curves", represents a solution in the database. On one curve of this array of curves, a point is selected as a starting point. The system associates a straight axis extending through the starting point to this point. The straight axis intersects the selected curve at the starting point or vice-versa, the starting point defines both the position of the axis and the selected curve. A straight portion of sufficient length is also understood as an 'axis'.

Around the starting point, a control region (as a navigation portion or window) is identified which is perceived by the user "as optically highlighted". This effect can be achieved in a number of ways, such as different color, different contrast, bolder line or different line shape (dots, dashed etc.).

There is a plurality of variants of optical highlighting.

An upper limit and a lower limit can be highlighted (by symbols, such as circles, dots, squares or stars), the control region can be highlighted by a thickening on the straight axis or this control region is represented in a different color than the residual portion of the straight axis. Or else, the portions outside of it are shown brighter or "greyed out" (a low-contrast or fainter grey value).

The variety of solutions stored in the database is visualized to the user by "effectively optically highlighting" this control region (portion). He is put in a position to control the representation of this variety and select therefrom for display thereof. Therefore, it is referred to as a "controllable visualization" which is not only a representation as such, but puts the user in a position to modify (control) the representation such that he is able to navigate in the variety of solutions stored in the database via the displayed DVH diagram. This is a powerful control via an inconspicuous DVH diagram portion which is instinctively understood by the user/planner.

The variety of currently non-displayed solutions (all solutions stored minus the one solution represented in the main diagram) can thus be visualized. The variety is not yet displayed, since only one of the variety of solutions is represented in the main diagram, but it is indicated by the control region located around the said starting point and highlighted in an optically effective manner.

In addition, it is to be said that the selected DVH curve (also graph or function) is the one determining the DVH curves in the stored, currently non-displayed solutions. These are the DVH curves corresponding to the selected DVH curve. All these curves also intersect the determined straight axis and all these points of intersection define the highlighted region.

One possibility of limiting this region at the top and bottom is to take the greatest and the smallest value of the final value and highlight this portion (upper limit, lower limit, highlighting, different-color display). Thus, the variety of solutions is represented, with respect to the selected DVH curve, in the highlighted region referred to as "first control region" (also: navigation portion).

It should be understood that other DVH curves can also be selected from the array of curves, wherein the highlighting of the first control region (navigation portion) is implemented in the same way. A plurality of selections can take place so that a plurality of DVH curves comprise a plurality of highlighted regions which are each located on a different straight axis (claim 6, claim 23). Preferably, all these axes (axis portions) are parallel and preferably all these axes (axis portions) are also oriented in a vertical direction. In a further embodiment, individual axes (axis portions) can also be oriented in a horizontal direction.

Each highlighted region represents the variety of solutions in the database, which are stored therein for the user, but not yet completely represented in the DVH diagram as the respective solution. The user is thus in a position to consider the variety of solutions based on one (or a plurality) of the DVH curves with a special focus on one of the curves of the DVH diagram, wherein this one curve of the array of curves corresponds to one of the volumes. In one example, the target T can be viewed and the variety of solutions can be evaluated by means of the target DVH curve.

Evaluation itself is not the subject matter of claim 1 and claim 25, rather the respective claim includes the representation enabling such a (human) evaluation. In order to be able to perform this evaluation at all, a comprehensible, analytical and clear representation is required not demanding too much of the user, however, providing him with sufficient information to enable him to make decisions. A clear technical challenge.

This includes the post-calculation of intermediate solutions (so-called recombination, claims 10, 15, 16) or an extension (claims 11, 19, 22) expanding the control region at the top or bottom (in the case of vertical straight axes). Control elements (claims 13, 17) assist navigation. This can be a selector which forms a point of intersection on the straight axis and which can be handled by a mouse pointer. This can also be a restrictor which reduces the control region in size (in length in the longitudinal direction).

This embodiment also designates the residual DVH graphs which are also calculated and represented. The embodiment is an extension of the idea to the case of a plurality of axes by observing restrictions existing on an axis on the respective other axes when re-calculating solutions per extension.

The maximum displacement movement of a selector (starting or intersection point) to be set arises from the mentioned restriction.

These control elements enable control of the change in representation. The represented solution is changed to a different represented solution, for example, when the selector, as a starting point or point of intersection of a DVH graph with a straight axis, is changed. The other DVH graphs follow this change since they are associated, as a solution, and represented with this graph currently set by means of the selector (for representation).

BRIEF DESCRIPTION OF THE DRAWINGS

Embodiments of the claimed invention are explained by reference to the Figures.

FIG. 12 illustrates the mode "navigation" (=nav) and reduces the control region 76 of FIG. 11 to a reduced control region 76a, with respect to the DVH graph 60a.

FIG. 13 illustrates a reduction of the control region 72 of FIG. 12 by means of an upper control element 71e displaced downwards on the straight axis 71 and to be referred to as "restrictor" since it reduces the upper final value of the control region 72 and determines a reduced control region 72a.

FIGS. 15b, 15c, 15d
Illustrate, in a sequence of a plurality of diagrams, how a few stored and pre-calculated solutions a, b, c are turned into a plurality of solutions serving as intermediate points (interpolation values). This is implemented between the pre-calculated solutions in order to fill the existing gaps and to thus achieve a perceived continuity of navigation.

DETAILED DESCRIPTION OF THE INVENTION

Figure 1:
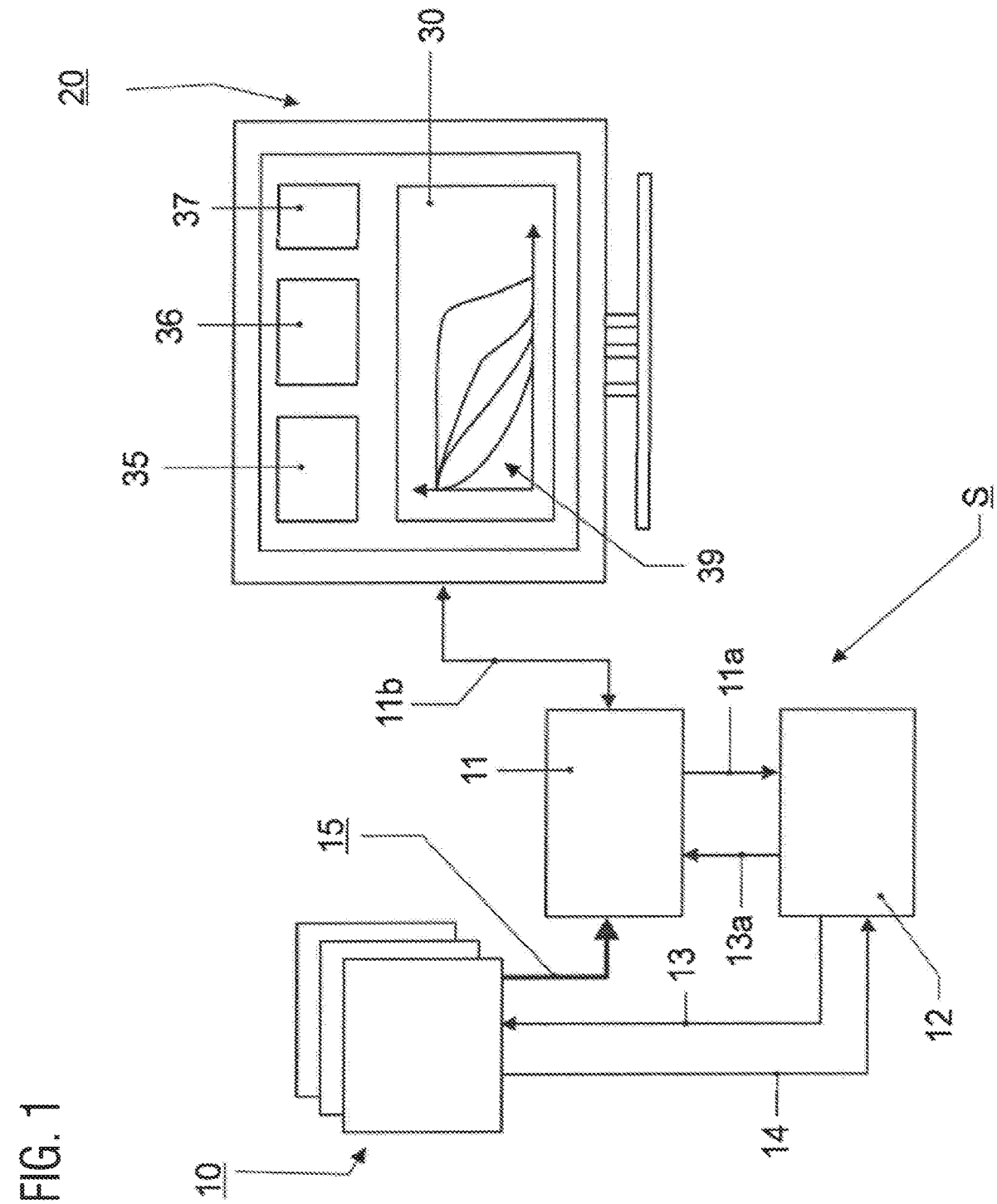
FIG. 1 is a system structure including components of the computer system controlling the display device 20. On the display device 20, a DVH diagram 30 is represented in the lower portion of the screen, the array of curves 39 of which represents the plurality of curves indicated in the DVH diagram 30 and associated with a single solution, wherein a variety of solutions is stored in the database 10.

FIG. 1 illustrates the system behind the screen display. The system S (on the left in FIG. 1) is the control technology responsible for the display device 20, i.e. a monitor, a tablet or other portable PC, or a screen display projected onto a canvas by a projector.

The display device 20 is insofar represented by embodiments as a user is to visually experience what pre-calculated solutions are included in the database, each of which comprising a plan of its own including a variety of technical parameters, which plan can be specified to a therapy device having a radiation head where these technical parameters then take effect.

It is not the subject matter of this description how the therapy itself is implemented, rather the subject matter is the way of handling the technical parameters representative for a respective therapy plan which, as such, are purely technical setting parameters of a technical device operating with technical parameters and comprising corresponding motors, control buttons and actuators exactly tracking the technical parameters once they are set.

Figure 2:
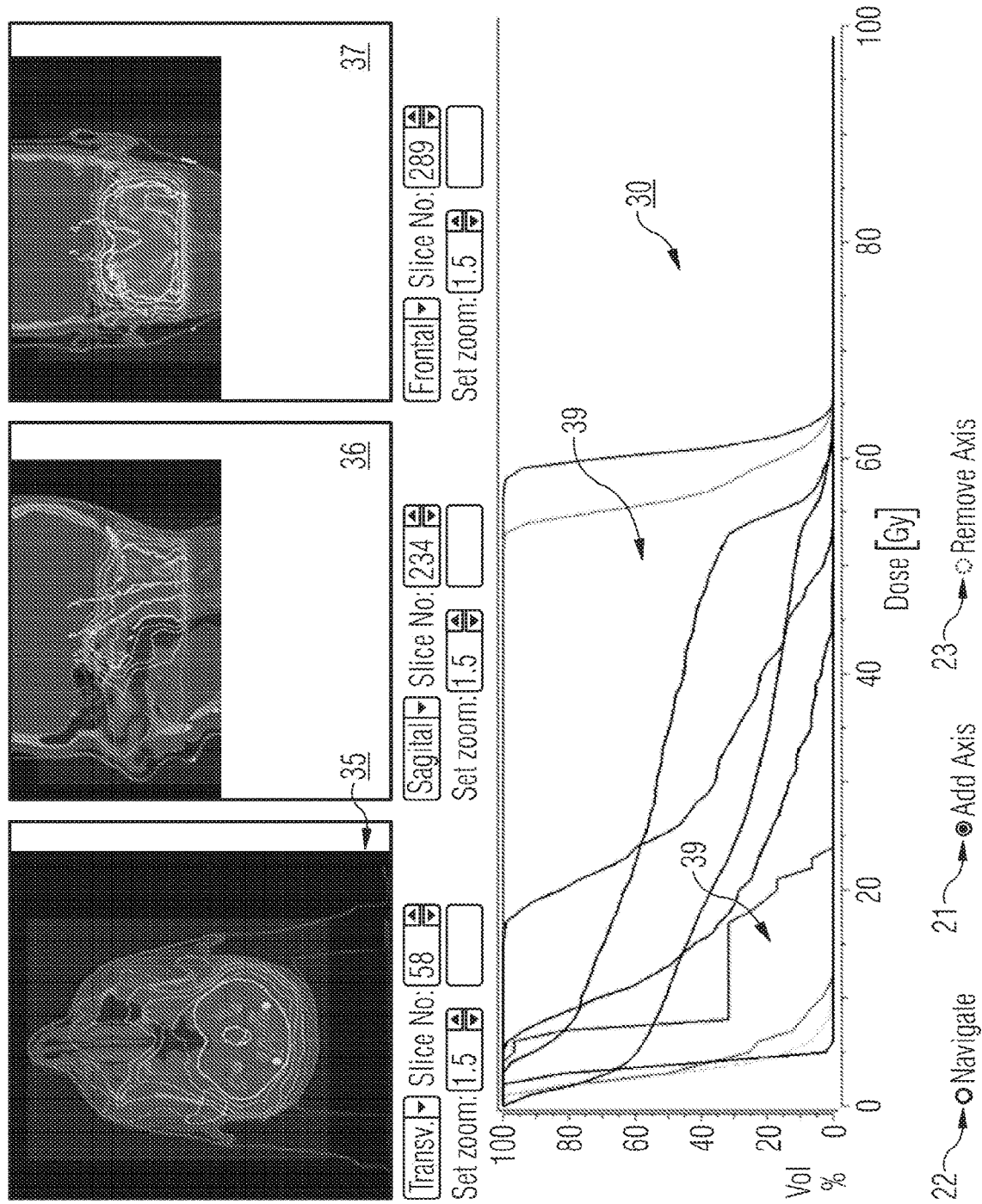
FIG. 2 is a cutout of the screen display 20 of FIG. 1 including the DVH diagram 30. The array of curves 39 can be seen here as well as the auxiliary views 35, 36 and 37 as three sections perpendicular to each other.

The display device 20, illustrated as a monitor here, comprises a display region, in which four portions can be seen. A lower, larger and square first region 30 is the DVH region visualizing a dose/volume histogram view. Two axes, x and y, are illustrated as a dose axis (in the x-direction) and as a percent-by-volume axis (in the y-direction). A plurality of graphs 39 are symbolically illustrated, which are dose/volume graphs of a diagram, the number of which corresponds to the number of those determined as defined volumes in a target area. Three auxiliary views constituting an example are disposed above the larger dose/volume diagram 30. In the example, these three auxiliary views 35, 36 and 37 are three sections, as is illustrated in FIG. 2, in a horizontal direction, a vertical direction and a direction vertically perpendicular thereto with respect to the target area in which the defined volumes are located. At least one of these volumes is a target represented by a tumor. At least one volume is a risk constituted, for example, by a sensitive organ or a sensitive tissue region. A further volume can be defined (but not necessarily) as a surrounding volume or a non-classified volume.

The control of the graphic representation operates with the controller S consisting of a visualization module 11 operating in the manner of an interpreter and in most cases also with a cache buffering the solutions read out from the database 10 via data path 15. The solutions are processed such that they are provided to the display device 20 via connecting line 11a as a screen signal. The screen signal yields the representation schematically displayed on the display device 20.

The visualization module 11 outputs the solutions either from the database 10 or from its own internal cache to the display device 20. When a requested solution is not present, the visualization module 11 requests a new plan via line 11b. The new plan is generated by the calculation module 12. This calculation is performed using already pre-calculated plans stored in the database 10 read out via access line 14. The calculation module determines the new plans which can be "recombined" solutions or completely new solutions which are not "between" but outside already pre-calculated solutions stored in the database.

These new solutions can either be buffered in a separate buffer of the calculation unit 12, or they can be stored into the database via memory line 13, from where they can be read out via access line 15 and supplied to the display device 20 by the visualization module 11.

In a separate, not shown embodiment, the calculation module 12 can also calculate intermediate solutions lying between two or between even more existing solutions which are not to be stored separately in the database 10, but to be supplied to the visualization module 11 via the direct path 13a in order to gain display speed.

The monitor line 11a is bidirectional for evaluating requests input by the monitor in the visualization module 11 and for revoking corresponding plans from the database or for causing calculation of said plans by the calculation module 12.

A plurality of plans, at least 20, however, in most cases several hundreds of plans, are held in the database, which plans have been pre-calculated as finished solutions in a calculation system not shown here and are capable of representing multi-criteria optimized (MCO) solutions. With respect to acquirement of such plans, it is referred to the US patent referred to at the beginning which also mentions other references as to how these pre-calculated plans are generated, obtained and stored.

Control of the display device 20 and control of representation of the variety of solutions in the database is to be the subject matter of the further Figures. This control of the variety of possible solutions can also be understood such that a type of navigation is to be enabled which operates interactively. The described system is also a planning tool for interactively selecting suitable solutions in the sense of therapy plans which are each composed of a number of technical control parameters. The graphs displayed on the monitor 20, in particular in the area of the dose/volume histogram 30, and represented in their entirety by 39 are used for navigation.

A more detailed illustration of this plurality of dose/volume graphs 39 is shown in FIG. 2.

Portion 30 in the lower screen half is apparent therein. Percent by volume is plotted on the vertical axis and dose is plotted on the horizontal axis. A plurality of graphs are apparent, some of which dropping very steeply at a very early stage and others dropping at a very late stage only. The right-hand graphs dropping at a late stage are those representing the undesired tissue zones, i.e. the target (tumor). The graphs dropping at an early stage represent the endangered risk organs. The organs are illustrated in the three sectional views 35, 36, 37 in three sections perpendicular to each other. They are characterized by outlines (also: contours) therein. Isodoses (lines of equal dose) are also illustrated which are indicated in the three sectional views. By means of selection buttons and selection zones, various layers (slices) available in the three planes can be selected. In the left-hand image 35, as a first auxiliary view, the transversal view can be seen. Therein, slice 58 is shown with a magnification factor of 1.5. In the central, upper auxiliary view 36, a sagittal view can be seen with slice 234 and a magnification of 1.5. In the right-hand auxiliary view 37, a frontal view can be seen, it is slice 289 with a magnification of 1.5.

At the bottom of the Figure, mode selectors are shown for switching the mode of navigation present in region 30. Navigation can be activated by selector 22, addition of an axis can be defined by means of selector 21 and removal of an axis can be set by selector 23.

The mode of operation of this mode selection is described in the following.

A first overview is provided by FIG. 3 which is explained in greater detail in the following and is also simplified for the sake of illustration of the explanation. However, the plurality of dose/volume graphs 39 can analogously be applied to the other images, wherein only three graphs are assumed to be present in the further explanation, and wherein the left-hand upper auxiliary view shows a simplified shape of the volumes to be viewed.

Figure 3:
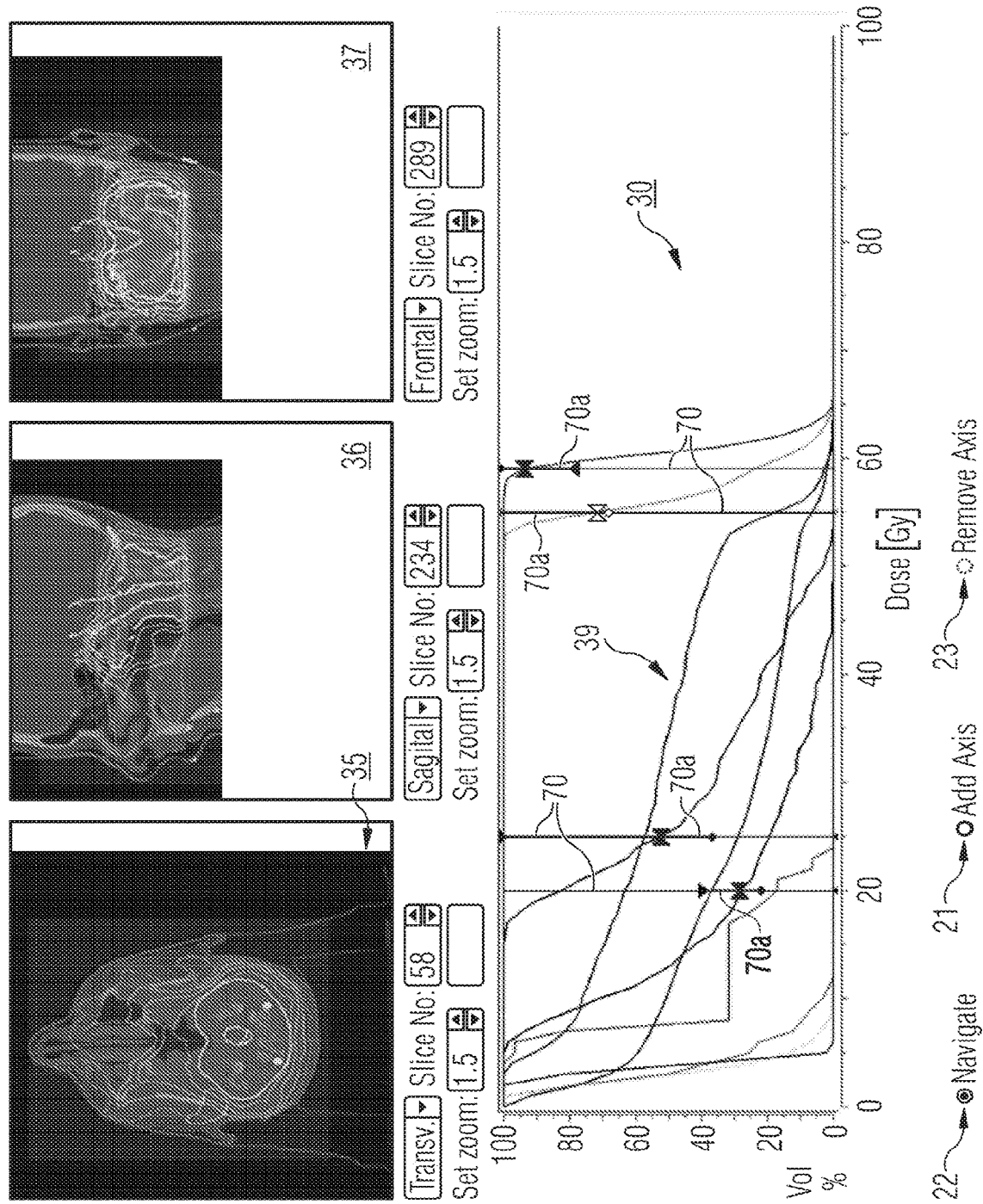
FIG. 3 is the DVH diagram 30 of FIG. 2 comprising visualizations of axes of a total of four planning criteria, one on each of two parotid glands and one on each of the two tumor volumes, all of them are to be seen as examples of volumes under consideration.

FIG. 3 shows the same views as FIG. 2, the only difference being that additional vertical straight axes 70 are indicated, each of which intersecting at least one dose/volume graph forming a respective point of intersection. Below and above a point of intersection, i.e. "around a respective point of intersection", a region is defined or indicated by upper and lower limit values, which represents a control region by means of which navigation is performed, as explained in greater detail in the following.

It should be noted that the three shown upper auxiliary views 35, 36 and 37 may also involve other ways of representation, for example, a three-dimensional view in only one image which can be rotated, pivoted or tilted in various axes for conveying or visually representing the solution set in the dose/volume histogram 30 to the user in a different way. Navigation, which is explained in the following, is apparent from the control regions indicated as a longitudinal portion on the vertical axis 70 around a respective point of intersection with a dose graph.

The control portions 70a are effectively optically highlighted relative to the rest of the straight axis 70 and visualize the variety of solutions not shown but present. They are present in the database 10 and can be displayed directly on the monitor 20 in the dose/volume histogram 30 via the visualization module 11, when the point of intersection, which is also called selector, is "displaced" within the control portion 70a defining the upper and lower limits of a displacement. The upper and lower limits can also be displaced (also called: restrictor), a further type of navigation. Thereby, the control region 70a is reduced in size. A further type of navigation is changing the smaller control region 70a into a new control portion, i.e. above the upper final value and/or below the lower final value, which portions have not been available for changing the position of the selector so far, but which will then be a point of intersection between the newly calculated dose graph and the vertical straight axis 70. This enlargement is called extension.

"Recombined" solutions, which are also present, but are re-calculated between solutions stored in the database 10, can be added to the visualized variety of solutions. They can fill the control portions 70a with further values, as is explained in the following.

The outlined navigation in one or more control regions 70a, which are therefore also referred to as navigation portions or navigation windows, is apparent from the simplified illustration of the following Figures.

Figure 4:
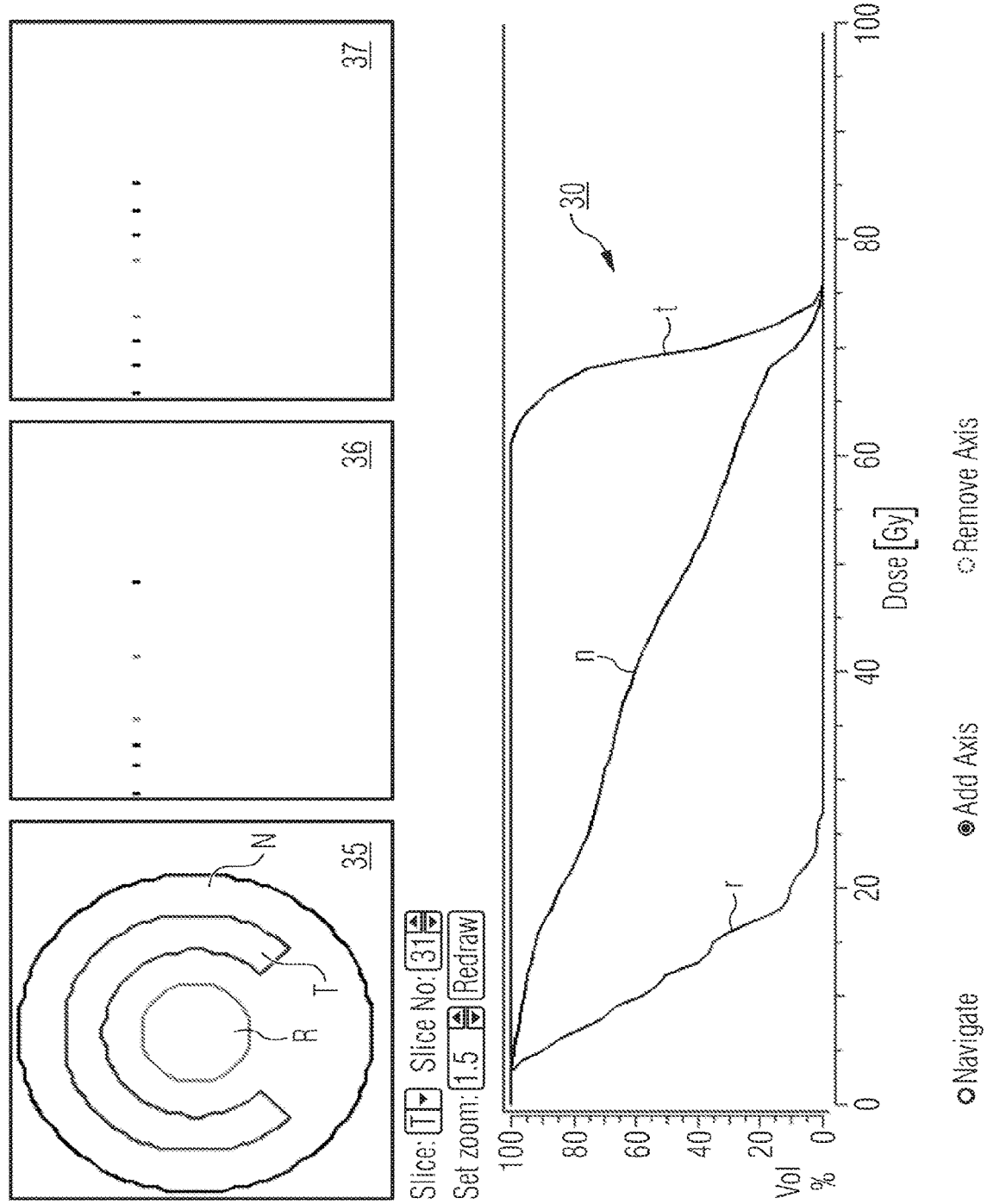
FIG. 4 is a simplified illustration for explanation of the system of FIGS. 1 to 3, wherein only three curves of a DVH diagram 30 and the configuration of the viewed volumes R, T and N are shown. Volume R in the center is the risk (an organ to be protected), the tumor is T, which is placed around the risk in the shape of a horseshoe in the simplified example, and the residual region outside of the two described regions R and T is the non-classified region N, which also forms a volume represented in the curves of the array of curves 39. Corresponding to the simplification in shape of the volumes, only three curves can be seen in the DVH diagram 30, which are associated with r (for the risk R), n for the non-classified region N and t for the target volume T.

The simplification is explained by means of FIG. 4. For this purpose, the volume is assumed to be planar, i.e. two-dimensional, as shown in the left top partial image (also called auxiliary view). Three volumes are shown in portion 35, the risk R in the center, the target T located around it in the shape of a horseshoe, and the non-classified portion N therebetween and outside of target T, see FIG. 6, portion 35. The other two sectional views perpendicular thereto each yield a line (or several points on a line) of no informative value. Associated with the defined volume regions of the flat disk shown in auxiliary view 35 are the three dose graphs in the DVH diagram 30: The left bottom graph r dropping at an early stage represents the risk. The central graph n substantially extending 45° from the left top towards the right bottom represents the non-classified region N located outside the risk and outside the target, as shown in auxiliary view 35. The graph dropping at a late stage only, extending at 100% far to the right up to 60 Gy is t and represents the dose for the target T. These three graphs are associated with the viewed volumes R, T and N. They represent a solution completely shown in FIG. 4 in the area of the DVH diagram. Other solutions are not shown, they are located in the database 10 of the controller S for screen display.

In FIG. 4, the representation is prepared for addition of an axis (mode: add) which is added as a straight axis 71 corresponding to axes 70 of FIGS. 2/3 in such a manner that it forms a straight line extending parallel to the y-axis of percent by volume.

This is to be explained with reference to FIG. 6. Before that, it is apparent from FIG. 5 that the two lines 36a and 37a are sections perpendicular to image 35. Here, the indicated volumes are provided with isodose lines corresponding to the graphs r, n and t in the DVH diagram 30 displayed or visualized on the display device 20. Also in this case, the system is prepared for inserting a straight axis corresponding to axis 70, which is then exemplarily implemented by means of FIG. 6.

It is to be noted once again that the three graphs of the DVH diagram view 30 constitute a simplified representation only which can and, in the practical case, will definitely take the form and shape of FIGS. 2 and 3, however, the three dose/volume graphs and the associated viewed volumes are entirely sufficient for explaining the functionality of the DVH navigation.

Figure 6:
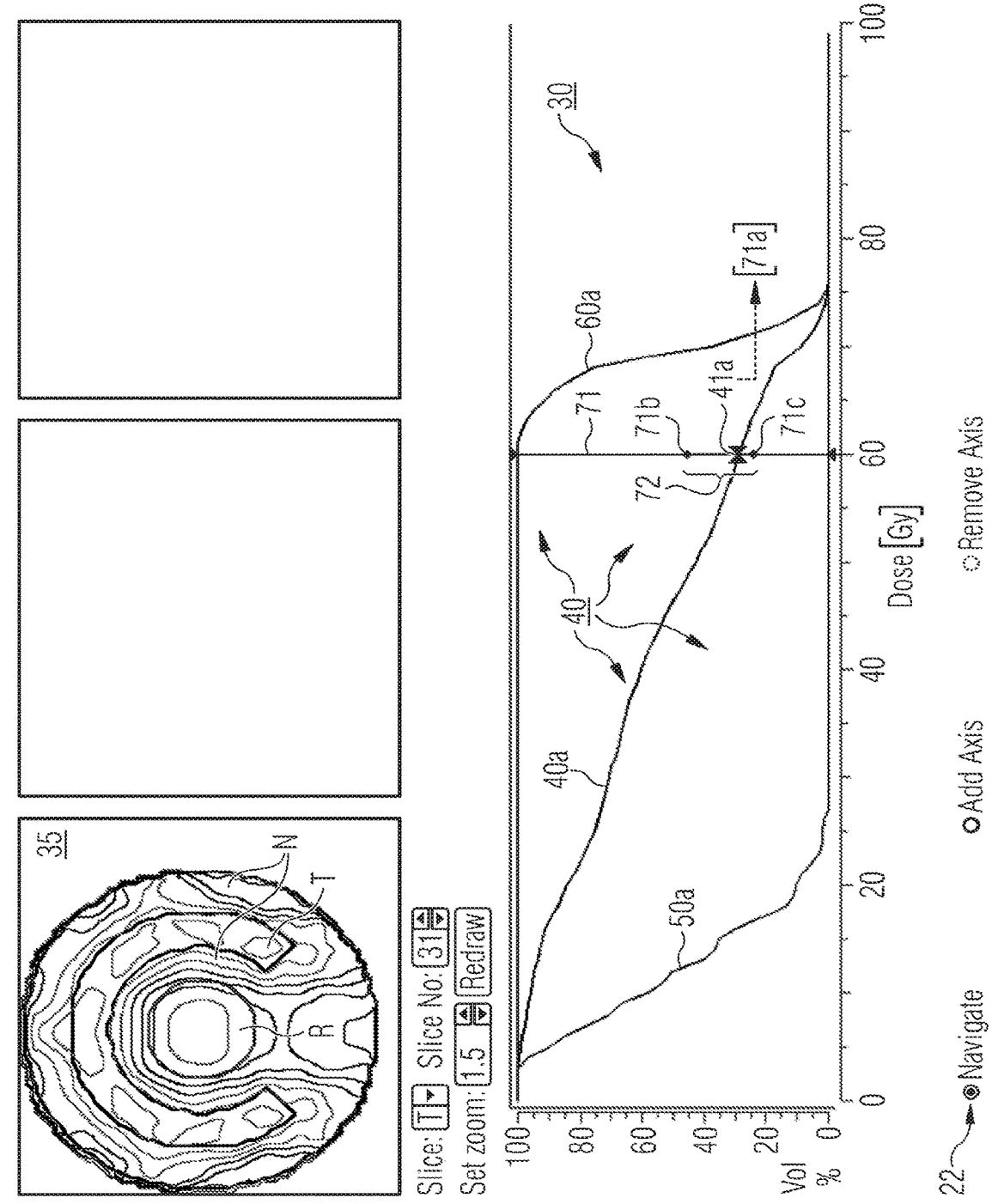
FIG. 6 is the illustration of FIG. 5, wherein control of representation is started oriented towards a determination of a point 41a on curve n. Notations r, n and t are abandoned here in favor of selected curve 40a and the other curves 50a and 60a associated with this solution, which curves are each part of a respective array of curves 40, 50, 60 provided by the variety of solutions stored in the database 10.
Figure 7:
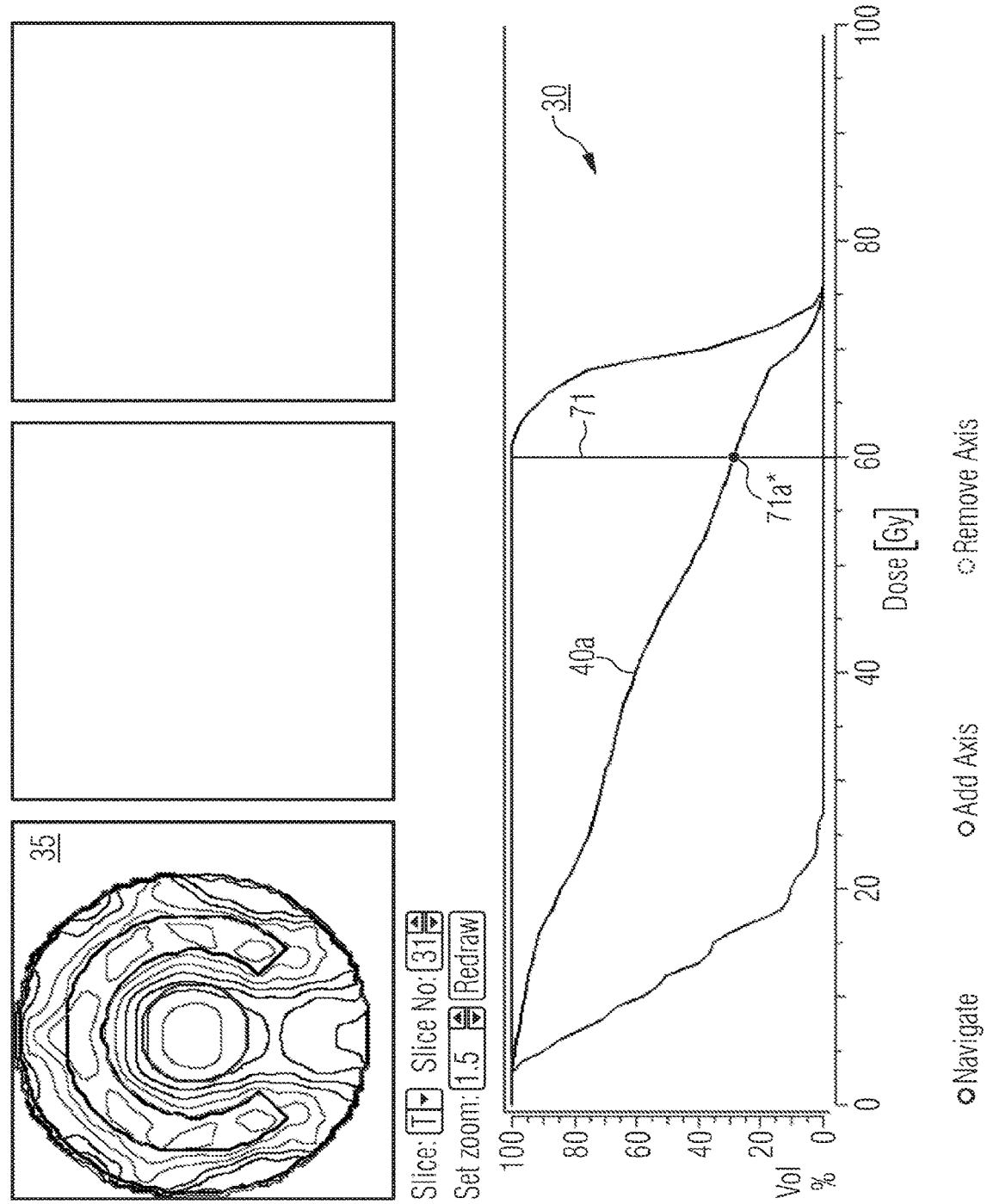
FIG. 7 is an illustration of the DVH diagram of FIG. 6, wherein the vertically oriented straight axis 71 is ready to be rotated. This is implemented about a pivot point 71a*.
Figure 8:
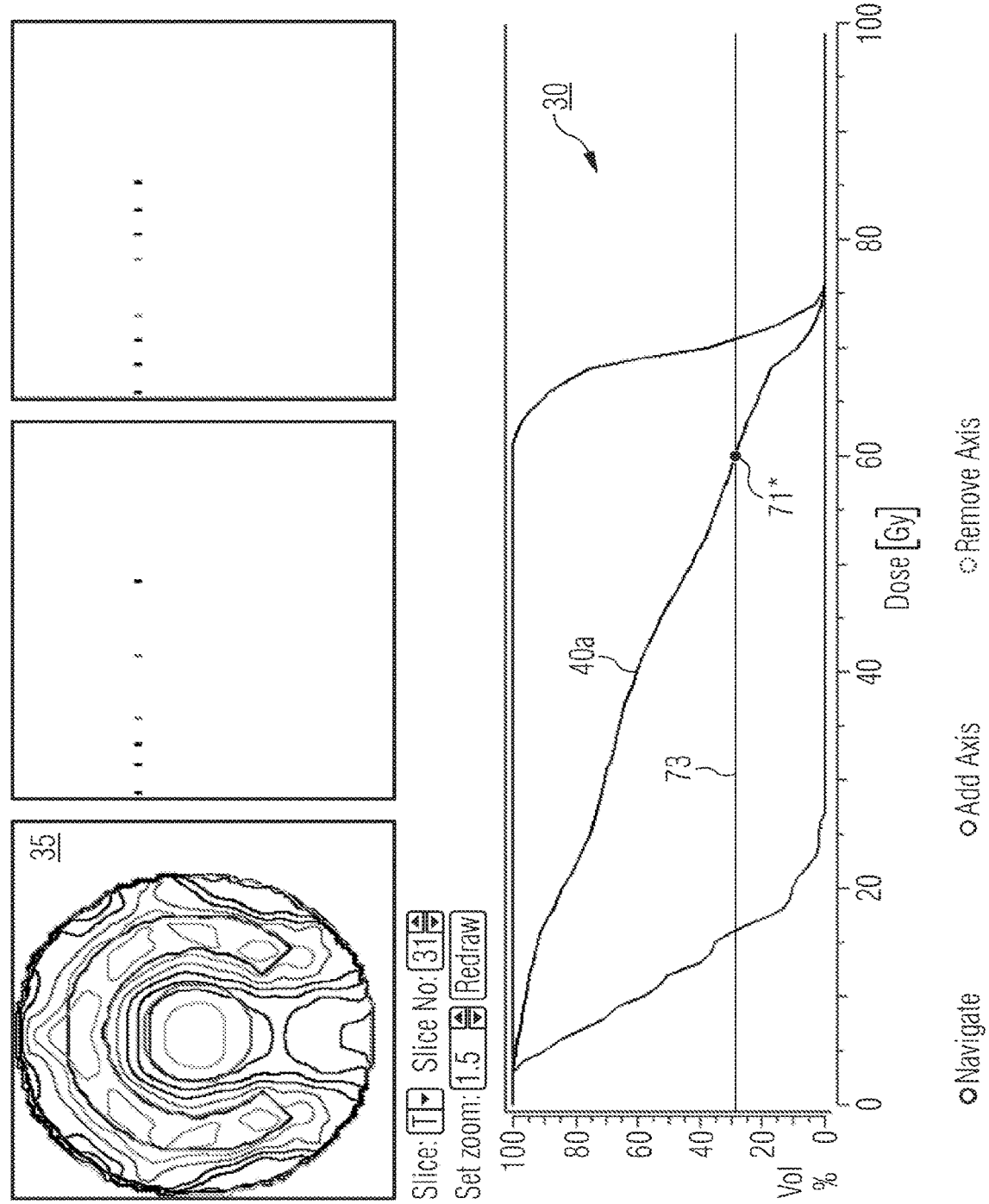
FIG. 8 is the state of FIG. 7 after rotation of the straight axis 71 for obtaining a horizontally extending straight axis 73 extending in parallel with the dose axis in the x-direction.

The solution shown in FIG. 6 including the three curves 40a (non-classified), 50a (risk) and 60a (tumor) is also illustrated in FIG. 7. In FIG. 7, the vertical axis 71 is modified. This can be achieved by some kind of activation performed outside the illustrated modes 21, 22, 23 (bottom of Figure), for example, by means of a right click on the point of intersection 41a or on the axis 71 itself. As a result, a symbol 71a* is illustrated indicating the option to pivot or rotate the axis 71. For example, it can be rotated in the manner illustrated in FIGS. 8 and 9 with respect to axis 73. The straight axis 71 then, as the straight axis 73, has a horizontal orientation.

Other orientations of the axis 71 are possible as well, intermediate positions between 90° and 0°, for example 40°, 50° or 60°. This angular range can be set in a plus or minus direction so that the vertical axis 71 can be pivoted by ±89° (with each intermediate value). The same point of intersection 41a (or 71a) as in FIG. 6 is achieved thereby, only with a different orientation of the straight axis.

Figure 9:
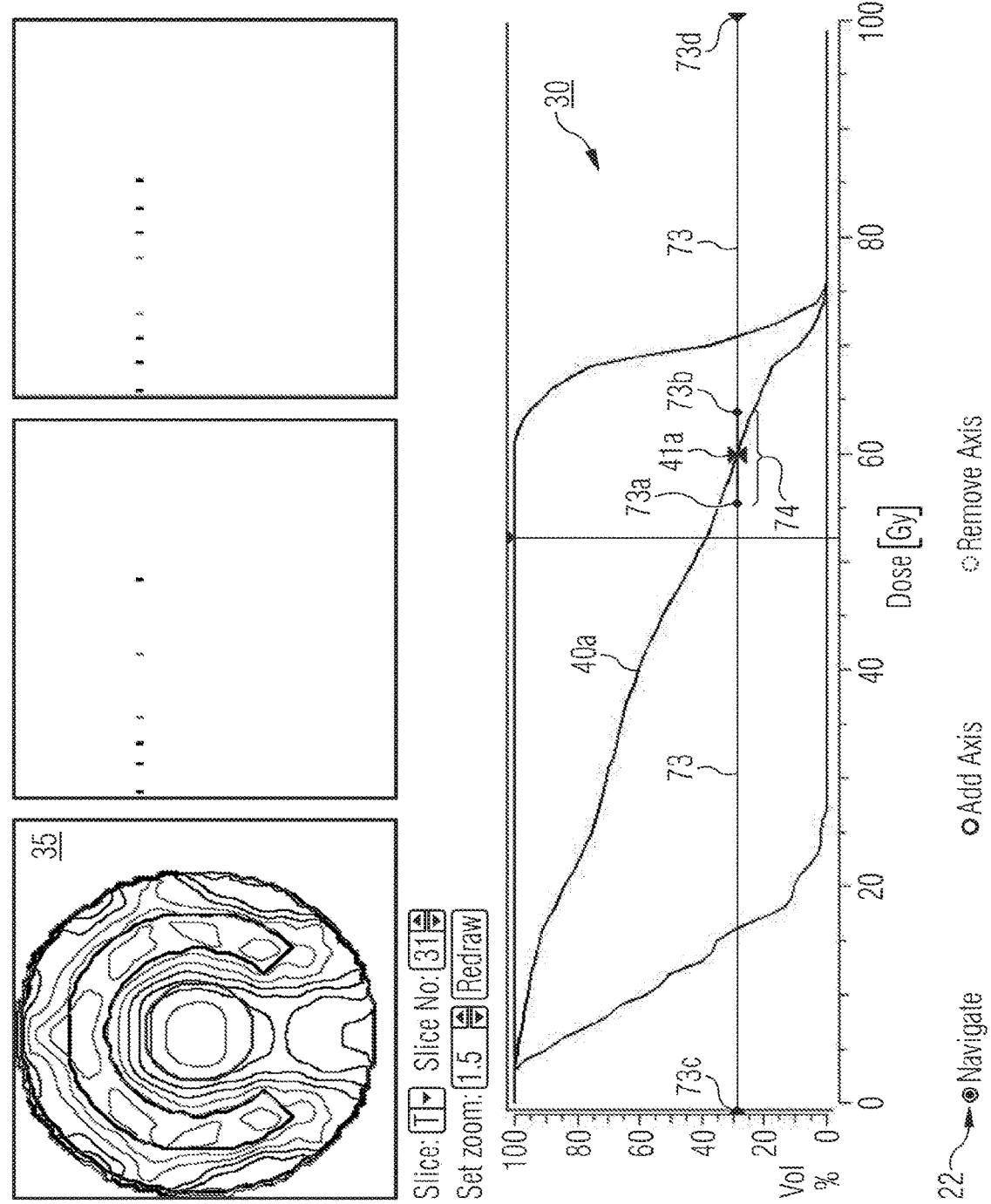
FIG. 9 is the illustration of FIG. 8 including a corresponding control region 74 located around the point of intersection 41a and formed on the horizontally extending straight axis 73 between 73a and 73b.

Correspondingly, a different control region 74 lying on axis 73 and representing the variety of solutions stored in the database is indicated in FIG. 9. Analogous to region 72 of FIG. 6, region 74 in FIG. 9 is configured as a control region or "navigation portion". The selected solution, which is solely illustrated in the DVH diagram, is the one shown in FIG. 6. The upper greatest value 71b and the lower smallest value 71c of the array of curves 40 (all curves 40a, 40b, 40c and more with respect to the stored pre-calculated solutions) here correspond to the left and right value 73a, 73b. With respect to the dose axis, they correspond to the smallest and greatest value, respectively. With respect to the surface area of the DVH diagram 30, they correspond to the left value 73*a* and the right value 73*b*. In FIG. 6, the upper and lower value thus correspond to the greatest and smallest value with respect to the volume axis.

The illustration of FIG. 9 is ready for navigation set via the control in the mode selector 22.

Figure 10:
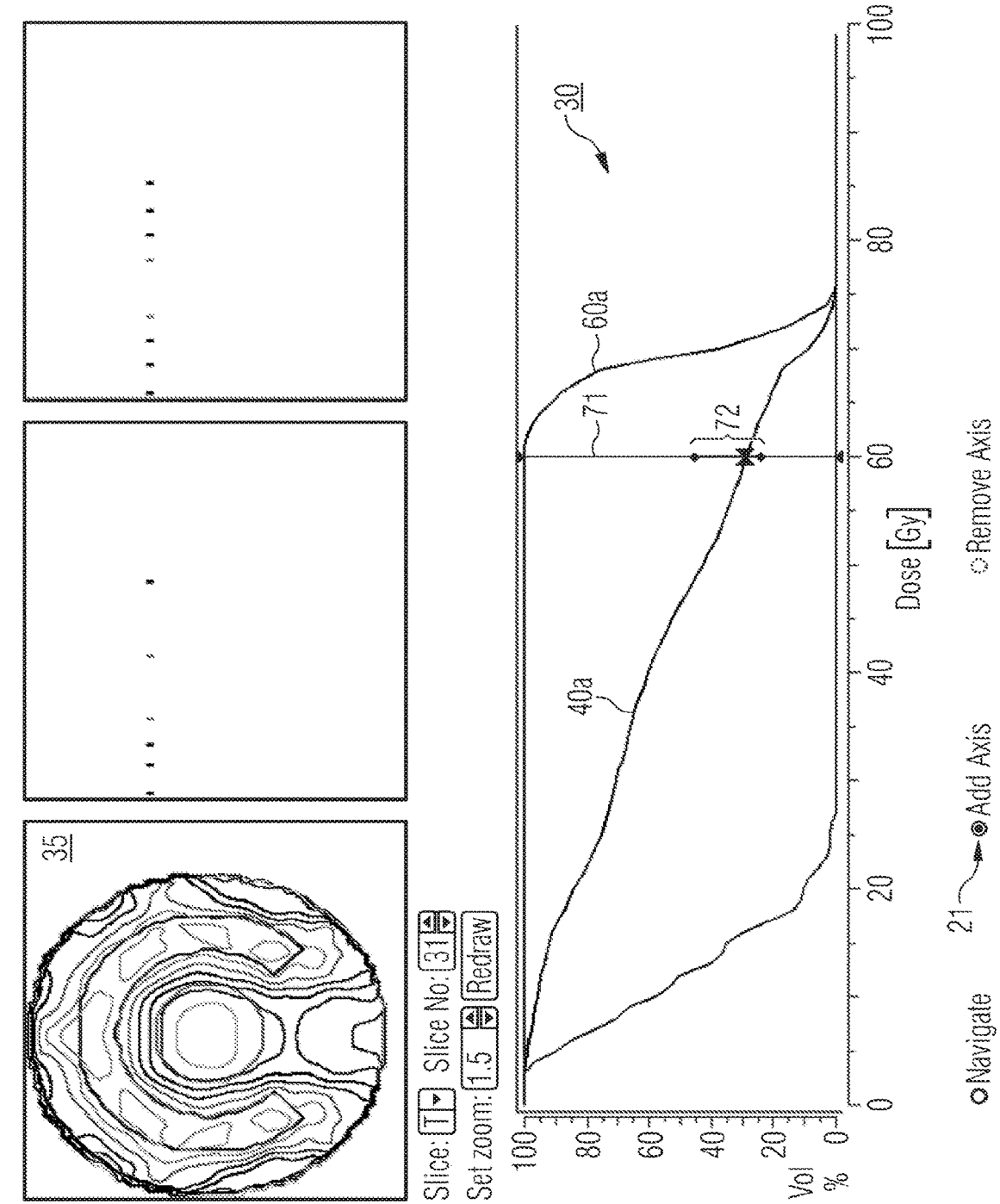
FIG. 10 is the illustration of FIG. 6 with a different mode "add an axis" (=add) being activated.

In FIG. 10, the representation of the DVH diagram returns to the representation of FIG. 6. Control activates the mode selector 21 permitting addition of a new axis.

An explanation of the three illustrated mode selectors is to be given here. The left selector 22 (as a radio button) enables navigation within a region, for example, the control region 74 in FIG. 9. Clicking on or activating the mode selector 21 enables addition of a further axis. This axis is defined at a point of intersection lying on one of the illustrated three DVH curves. The axes can be placed on different curves, however, a plurality of axes having the form of axis 71 of FIG. 10 can also be placed on the same DVH curve 40*a* as the selected curve. Then, they are spaced in the x-direction and have an associated control region each which is shown in a manner placed around the point of intersection and highlighted. The highlighting represents the variety of solutions stored in the database 10.

The third mode selector is the one for removing an axis. When it is selected, one of the axes placed in the DVH diagram can be removed. This will be explained later on when a plurality of straight axes will be present.

Figure 5:
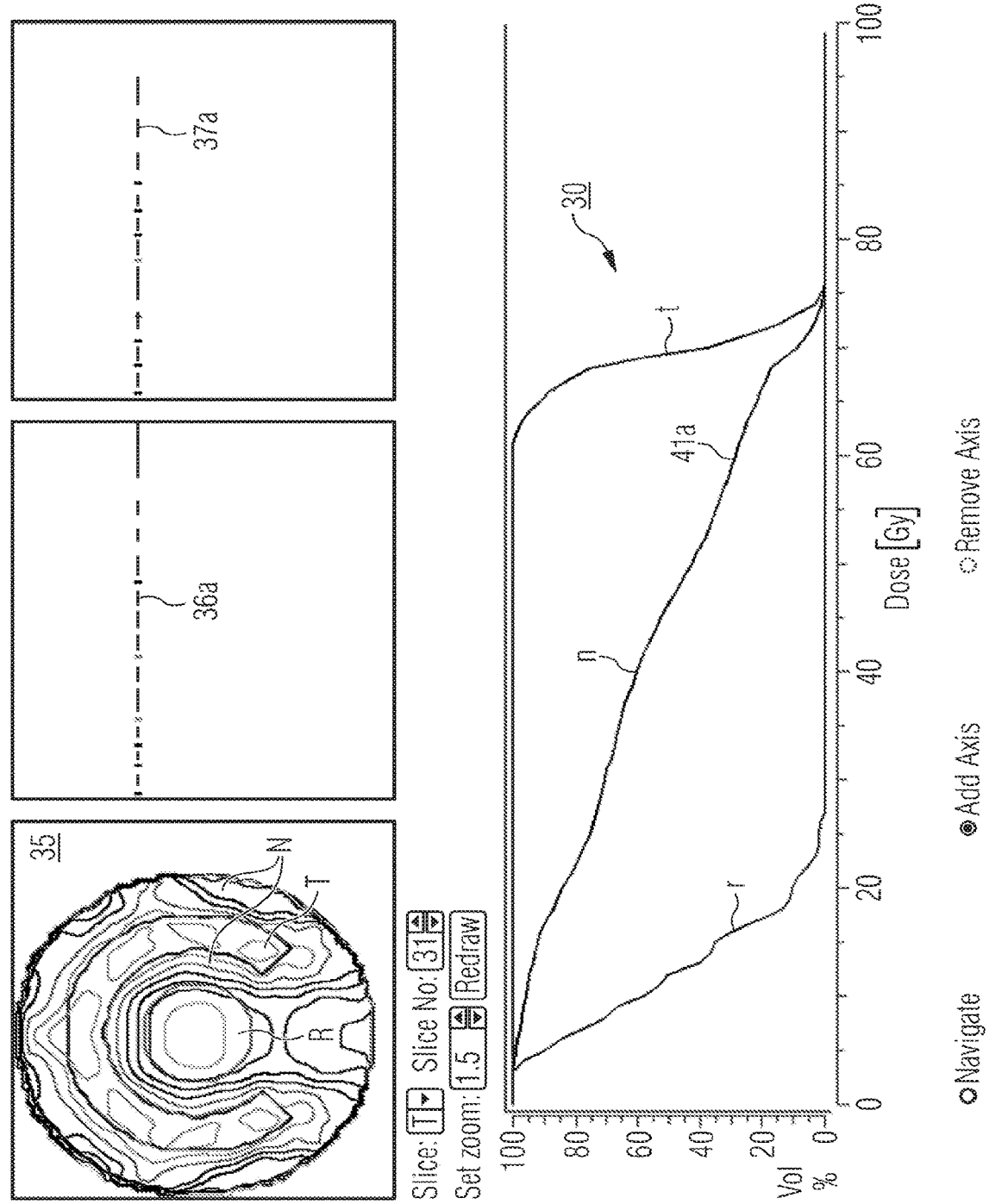
FIG. 5 shows the illustration of FIG. 4, wherein isodose lines are also indicated in the volume region of auxiliary view 35 which are part of the technical setting represented by three curves in the DVH diagram 30. The distance between the isodose lines is 10 Gy in each case. Due to the two-dimensionality of the viewed case, the two other auxiliary views 36a, 37a, which are oriented perpendicularly to view 35, are simple lines. They are of no informative value, which is a consequence of the simplification for the sake of explanation of the system.

In the example of FIG. 10, the axis 71 can be removed so that the illustration of FIG. 5 is obtained. In an example, removal of the axis is performed such that the third mode selector is activated and the axis to be removed is identified to the system, for example by clicking on some point on the axis. In the example, the mode selectors are configured as "buttons", however, they may also take a different form, such as a "drop-down menu", or these mode selectors are not explicitly shown and arise from an invokable context menu which opens, for example, when the user clicks on a neutral surface area in the DVH diagram 30 with the right mouse button in order to open the context menu, and selects one of the three described modes, i.e. navigation (nav), addition of an axis (add) or removal of an axis (remove). In a not shown embodiment, the respective then selected (active) mode can be illustrated as active by means of words in a clearly visible location of the screen. One type of illustration is: "now active", followed by the mode now being activated (nav, add or remove).

According to FIG. 10, the mode for adding an axis (by means of mode selector 21) is activated. This mode results in FIG. 11. This Figure illustrates the added further vertical axis 75 which is inserted by clicking on a starting point 61*a*. A point of intersection 61*a* of the DVH curve 60*a* with the added axis 75 arises in the solution shown in FIG. 10.

By determining the second starting point 61*a*, please be reminded that the first starting point was used 41*a* for determination of the first vertical axis 71, the navigation window (control region), which is region 76, is opened as well. It is located on axis 75 and has a maximum value and a minimum value with respect to the percent-by-volume axis. This control region 76 or second navigation portion (navigation window) is greater than the control region 72 of FIG. 10. It is located in the upper region of the percent-by-volume axis since it relates to the tumor characteristic. The point of intersection 61*a* indicates that more than approx. 92% is irradiated with a radiation dose of 65 Gy with respect to the tumor T in the left top auxiliary view.

The value range of the solutions stored in the database generated by the second control region 76 ranges from 44% to 100% of the percent-by-volume axis. The selector is at 92% and no restrictors are activated, which will be explained later on.

Figure 11:
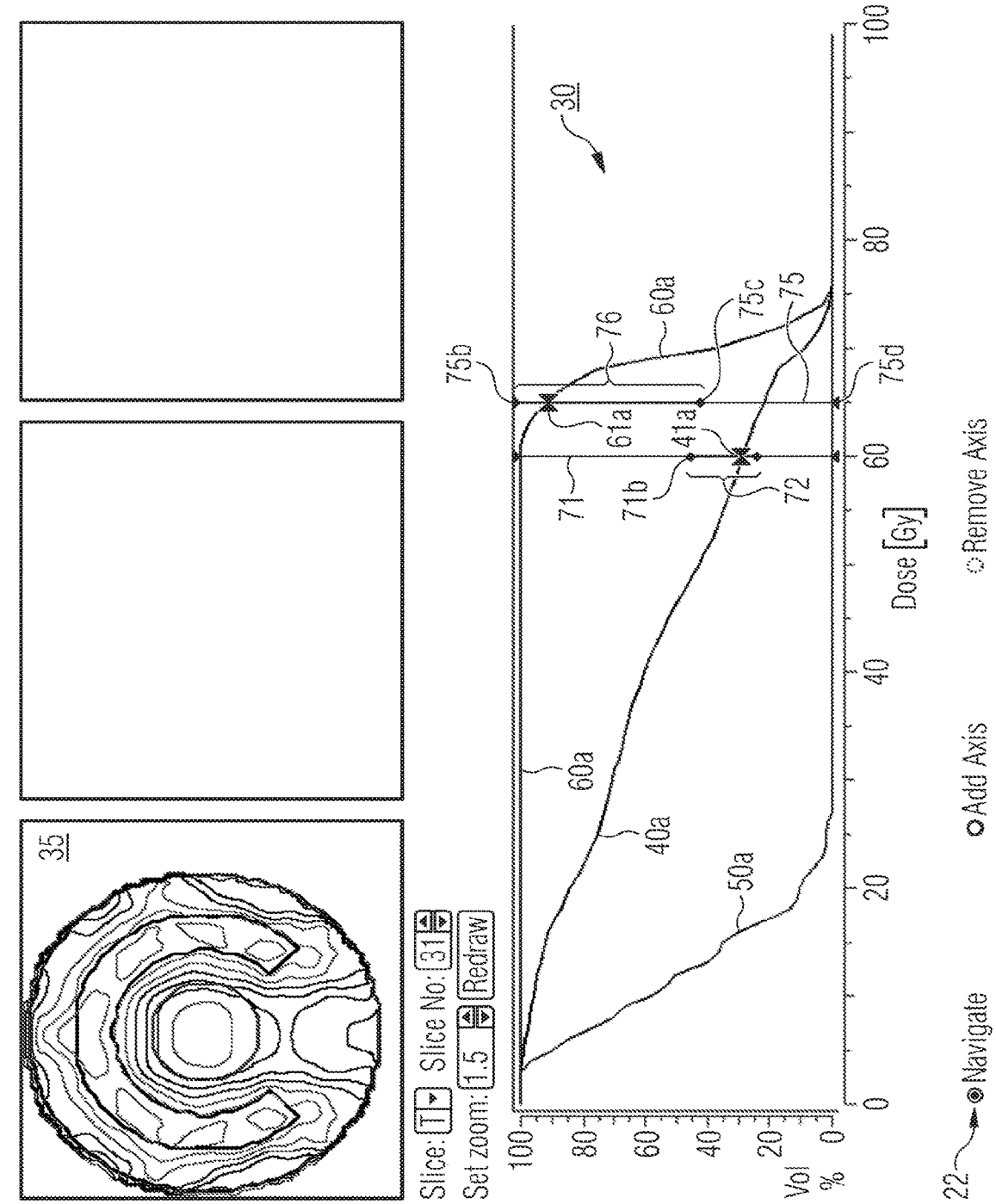
FIG. 11 is the added new straight axis oriented in the vertical direction and intersecting the DVH graph 60a at 65 Gy. The point of intersection 61a opens up a new control region 76.

In FIG. 11, the mode selector 22 is activated so that navigation is possible in the now formed two control regions 72, 76, which is explained in the following Figures. Both control regions 72, 76 represent the variety, or variety of stored solutions, only one of which is represented in the diagram 30 by three curves 50*a*, 40*a* and 60*a*.

Navigation is performed by changing the size of the control regions 72 and 76 or by displacing the points of intersection 61*a* or 41*a* within the respective navigation portion. Both actions, i.e. the specification of the limits of the navigation portions and the "displacement" of the point of intersection within the (specified) limits of the control region, are navigation actions and serve the purpose of identifying a solution from the variety of stored solutions.

Figure 12:
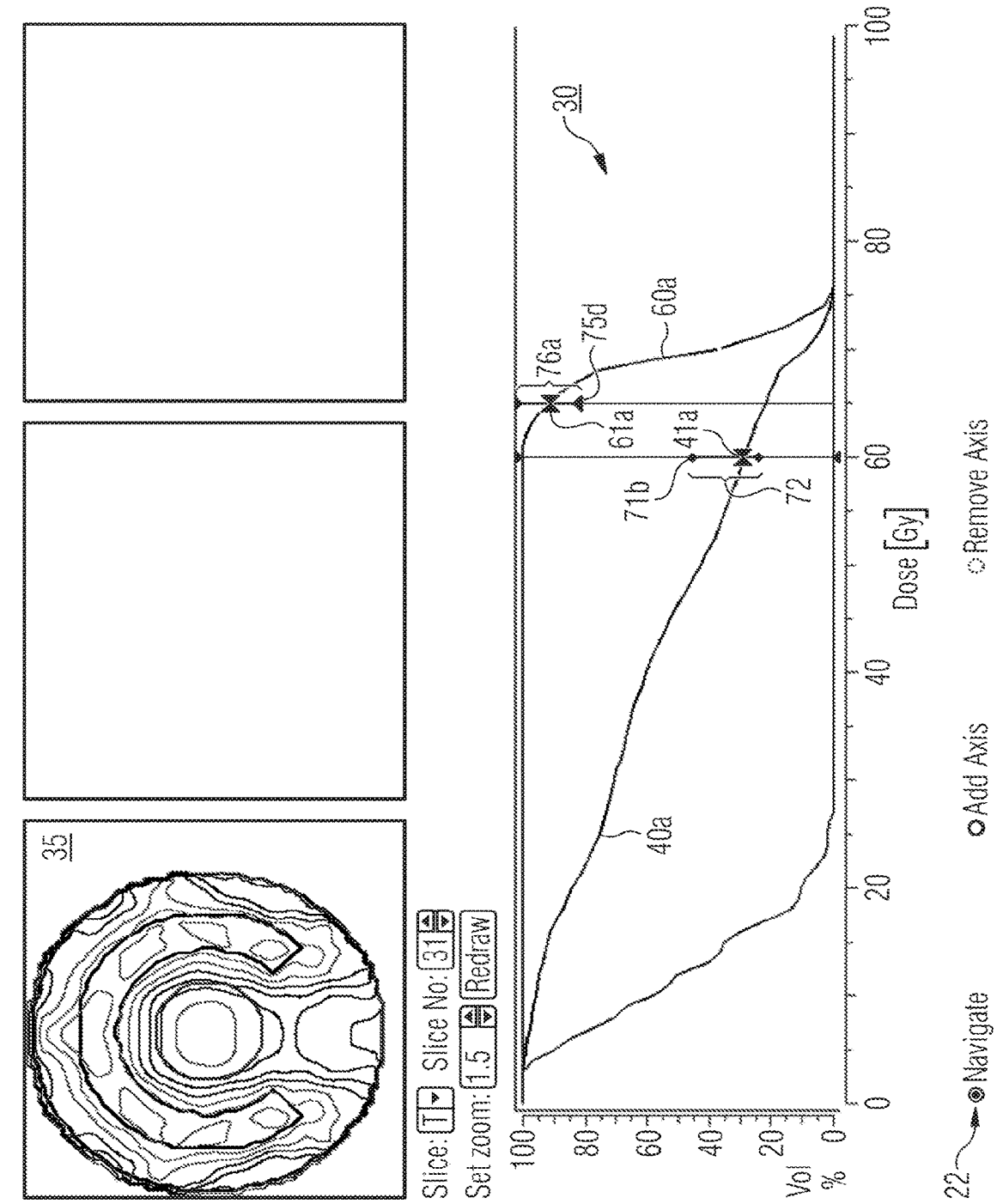
Figure 13:
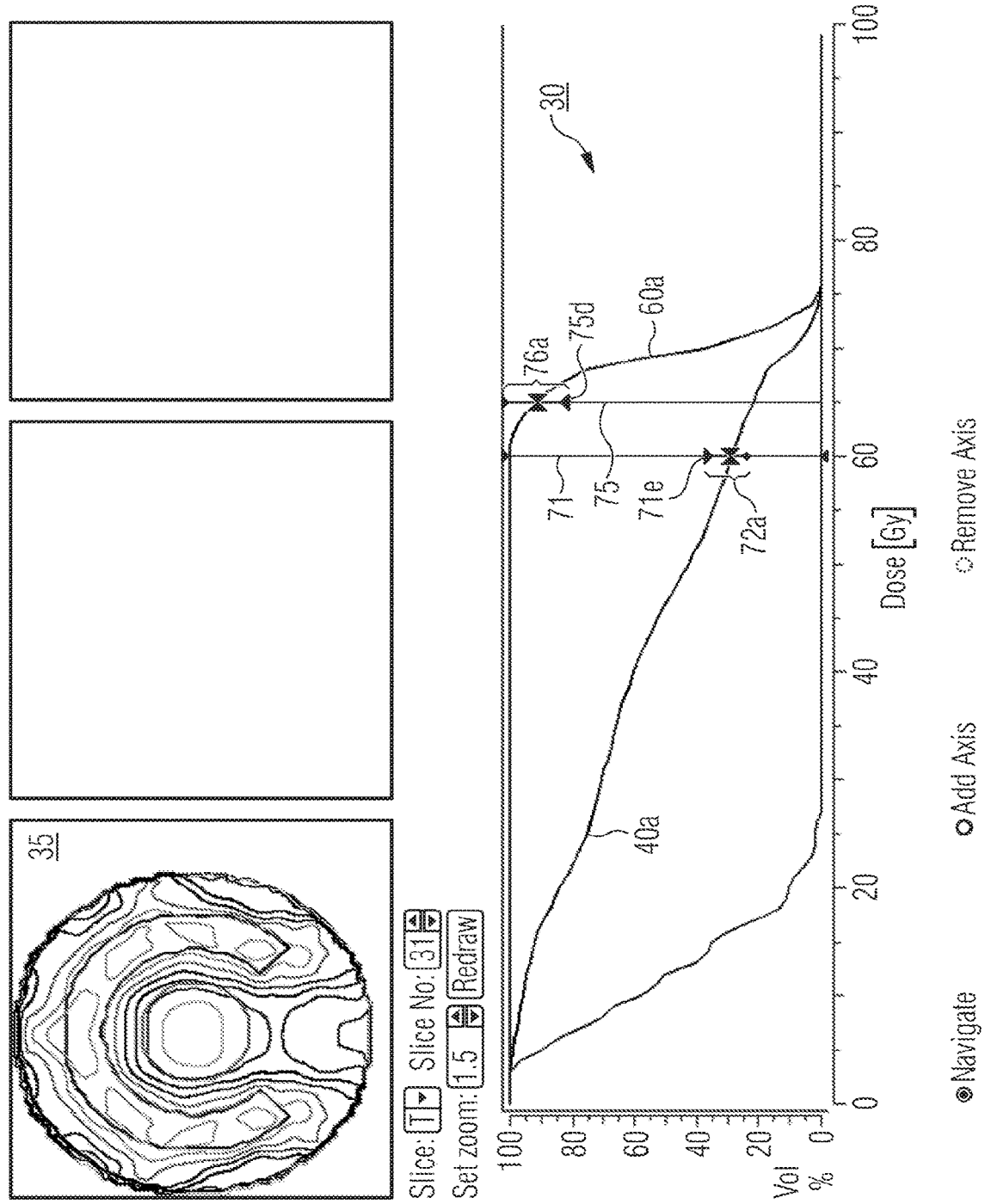

Two types of navigation are shown in FIGS. 12 and 13. They involve displacement of the lower or upper final values of the navigation portions 76 and 72.

In FIG. 12, the lower final value or the minimum value has been changed from value 75*c* of FIG. 11 to value 75*d* in FIG. 12. This lower limit 75*d* can arise either from the lower limit value, the minimum value 75*c*, or from the lower end of the straight axis 75, as symbolically illustrated in FIG. 11 in form of a vertically oriented wedge at the lower end of this axis. It is grabbed by the mouse pointer and displaced upwards on the axis until it reaches position 75*d* at 85% of the percent-by-volume axis. This newly formed navigation portion only has the size 76*a* as compared to size 76 of FIG. 11. It remains on the same curve 60*a* and at the same point of intersection 61*a* which has not changed.

Accordingly, the upper final value 71*b* on the first placed axis 71 can also be displaced, namely downwards in the example, which results in the new value 71*e* of FIG. 13. The region 72*a* thus reduced in size is formed and has an upper limit of 34 percent by volume.

By changing the two limits, both at the top and bottom, on two curves according to FIGS. 12 and 13, the representation on the respective other straight axis (the respective other "criterion") remains unchanged in the shown example.

However, changes to the upper and lower limits of the "nav-prt" (navigation portions) can also be made such that a change to the one portion also results in a change to at least one or both other limit value(s) on the other straight axes.

These changes in limit value on the other axes are caused by the fact that the points of intersection of solutions located on these axes, the points of intersection of which are located outside of the changed "nav-prt" on the starting axis, are removed from the navigation regions, as nav-prt, on the other axes. When one of these points of intersection forms a limit value for a navigation region (nav-prt) on another axis, removal thereof from the nav-prt results in the said change in limit value. This removal of points of intersection from the nav-prt on other axes has the effect that the change in starting values exclusively results in solutions, the points of intersection of which are located within the respective nav-prt on all axes.

Figure 14:
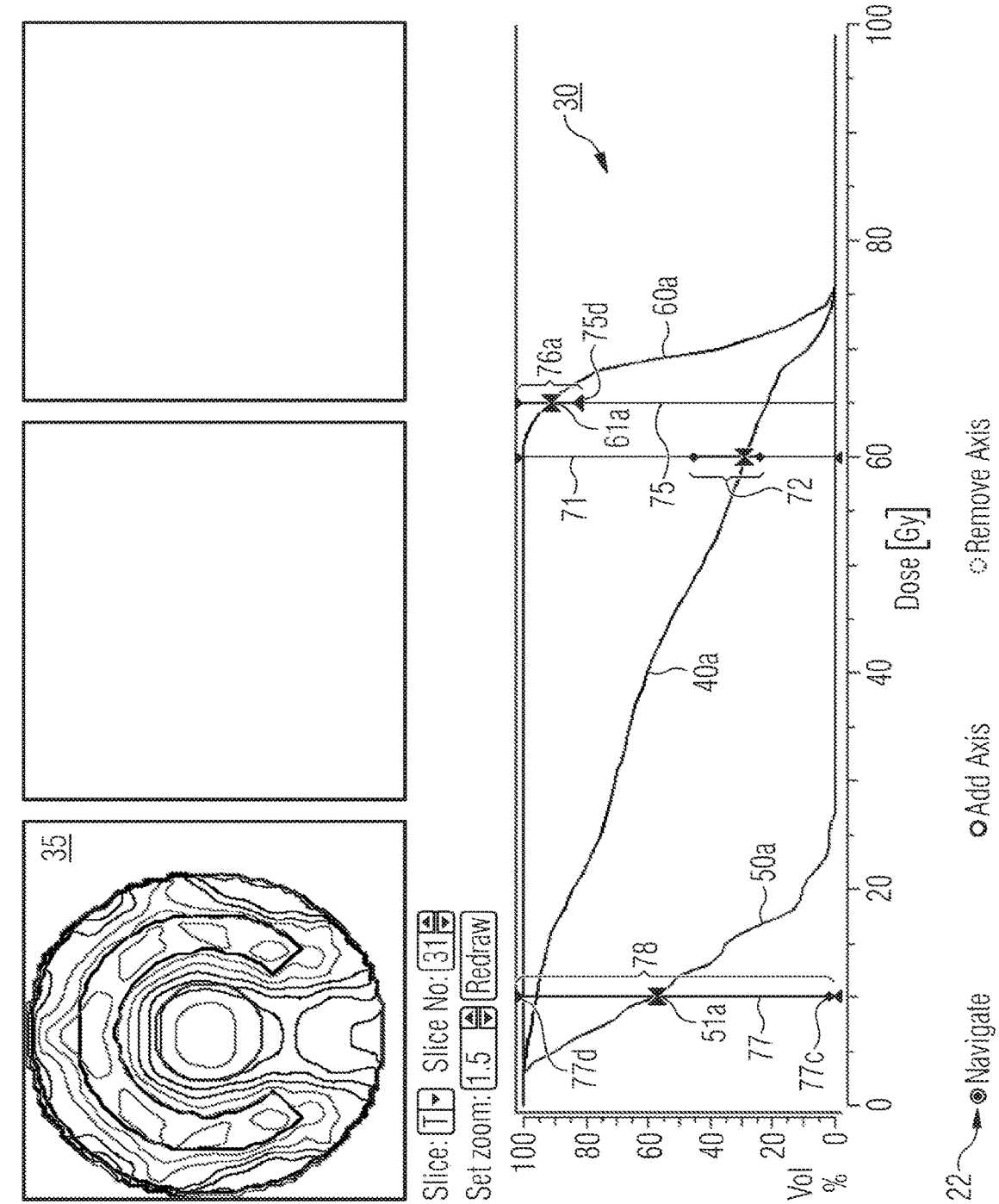
FIG. 14 shows an already added third straight axis which is oriented vertically. This straight axis 77 is associated with the third graph 50a in the DVH diagram 30.

FIG. 14 shows the addition of a further axis, wherein the mode selector 21 (add axis) has been previously activated. The newly inserted axis 77 is defined as a vertical axis and is determined by clicking on the point of intersection 51*a* on curve 50*a*. Since this curve represents the radiation exposure of risk R, it is located far in the left region of the array of DVH curves 39. The control region 78 thus generated between the upper and the lower limit, i.e. the greatest and the smallest value of all stored solutions for risk R. The greatest value is 77d (at 100%), the smallest value is 77c (at 3%), and the specified range 78 is a little less than 100%.

In the right portion of FIG. 14, the state apparent from the right side of FIG. 12 has been re-set. This state has a raised lower final value 75d on the target curve 60a and includes no restriction to the first control region 72 determined by the point of intersection 41a.

It is apparent from FIG. 14 that three vertically oriented straight axes 77, 71 and 75 are present, each associated with a different curve in the DVH diagram 30. This representation can also be modified, when two or more vertical axes are placed on a curve, for example the curve 40b lying between the two other curves. Then, different dose values are positions, which each cause a point of intersection formed between the curve 40a and each one of the vertical axes.

The vertical axes 71, 77, 75 mentioned in the description are graphically indicated on the monitor 20 and can be handled by the user via a mouse pointer or via a tablet, wherein actions are transferred to the system S of FIG. 1 underlying the screen display by means of direct contact.

These vertical axes can also be horizontal or can be pivoted, in accordance with the previous representation, about their point of intersection with the respective curve of the DVH diagram.

The axes may also be referred to as criteria. A criterion is, in a way, a planning aspect, according to which a user or planner can evaluate the quality of the plan (of technical control parameters) underlying the representation. The representation in the control region around the selected point on the selected curve is particularly helpful in this connection. This control range (the navigation interval) tells the user what options and scope are available to him for changing the currently displayed plan, thus providing him with a view on his options and making the planning options transparent to him. Or else, this control range, for example 72 in FIG. 14 or 76 in FIG. 11, shows him the options he may use when he is involved in changing the plan currently displayed.

Navigation portion 76 or portion 72 is respectively located on a vertical axis or line 71 or 75 and is thus the criterion or part of the criterion enabling improvement of a currently displayed plan, or by means of which the user wishes to improve the displayed plan.

The display of a further new plan, which is also stored in the database 10 in a pre-calculated state, is explained with reference to FIG. 15. Based on FIGS. 15a to 15d, the calculation of new solutions is described.

The starting point 61a of FIG. 14 is displaced upwards. It becomes the displaced starting point 61b (also shown as 61a') in FIG. 15. By use thereof, the curve is seemingly displaced, however, in reality another solution is displayed which consists of curves 60b, 40b and 50b and has been stored in the database.

Displacement can be implemented by grabbing with a mouse pointer or by direct displacement on a screen of a tablet.

By displacing the point of intersection 61b, which is actually not an upward displacement of the starting point within the navigation portion 76a, another plan having three dose/volume graphs is selected in reality. Point 61a can be displaced within this region 76a, between the upper final value 75b and the lower, upwards displaced threshold value 75d, to value 75f. One of these displacements is shown in FIG. 15 and represents a further solution including the exemplary three DVH graphs which is now displayed instead of the previous solution including the three graphs 40a, 40b, 40c, in case auxiliary views 35, 36 and 37 are also present, they are updated as well. In the example, mainly auxiliary view 35 is involved.

Figure 15:
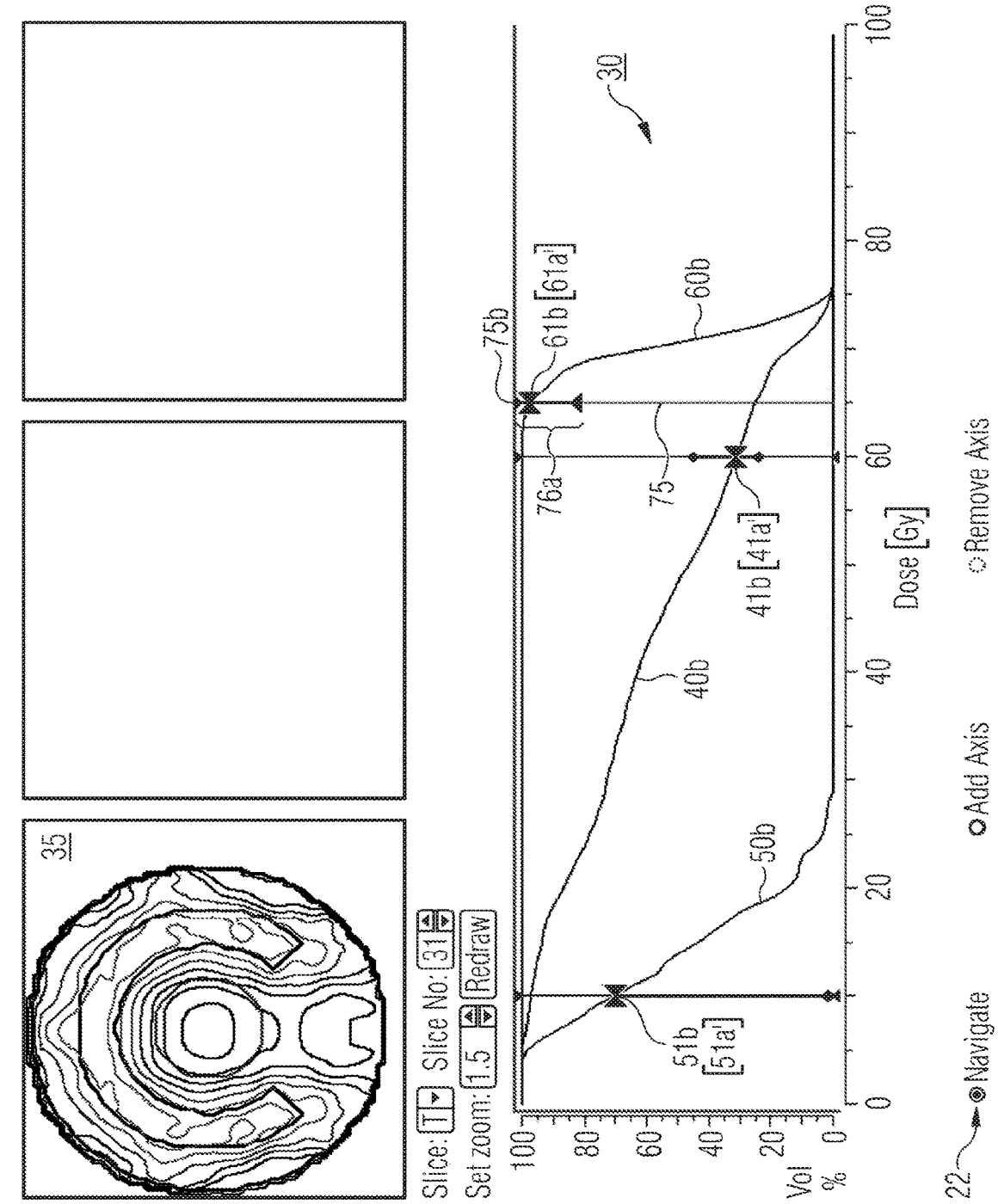
FIG. 15 illustrates the representation of a new plan (plan 'b'), which is selected by displacing point 61a to point 61b in the control region 76a and is then displayed.

Due to the "displacement" of the starting value 61a to the new displaced starting value 61b, the first starting value 41a in control region 72, cf. FIG. 12, is also displaced (changed) to the new displaced starting value 41b in FIG. 15. Accordingly, the starting value 51a of curve 50a is also "displaced upwards", when a new curve 50b with its "displaced" starting value 51b (also symbolized by the first starting value 51a displaced to 51a') is displayed.

Of the stored solutions, different further pre-stored solutions can be represented by "displacing each starting value" on each of the straight axes, which solutions are obtained in this way by representation of corresponding curve triples, for example 40c, 50c and 60c.

Reasonably, the displacement of the dose of the target in FIG. 15 is implemented such that an upward displacement also causes a higher exposure of the other viewed volumes R and N. Accordingly, all points of intersection of FIG. 14 are displaced upwards and are at a higher value in FIG. 15.

In numbers, the value 61a has been raised from 92% to 98%. The other three DVH curves are thus represented by the system S of FIG. 1 in an updated state. The risk criterion has been raised from 58% to 71%, the residual body tissue on curve 40b has been raised from 28% of curve 40a of FIGS. 14 to 32% in curve 40b of FIG. 15. It is to be emphasized that this raise is not a linear displacement, but is obtained by representation of a different, pre-calculated plan in the database. This new represented plan has the values 98%, 71% and 32% on the dose graphs 60b, 50b and 40b.

Figure 15A:
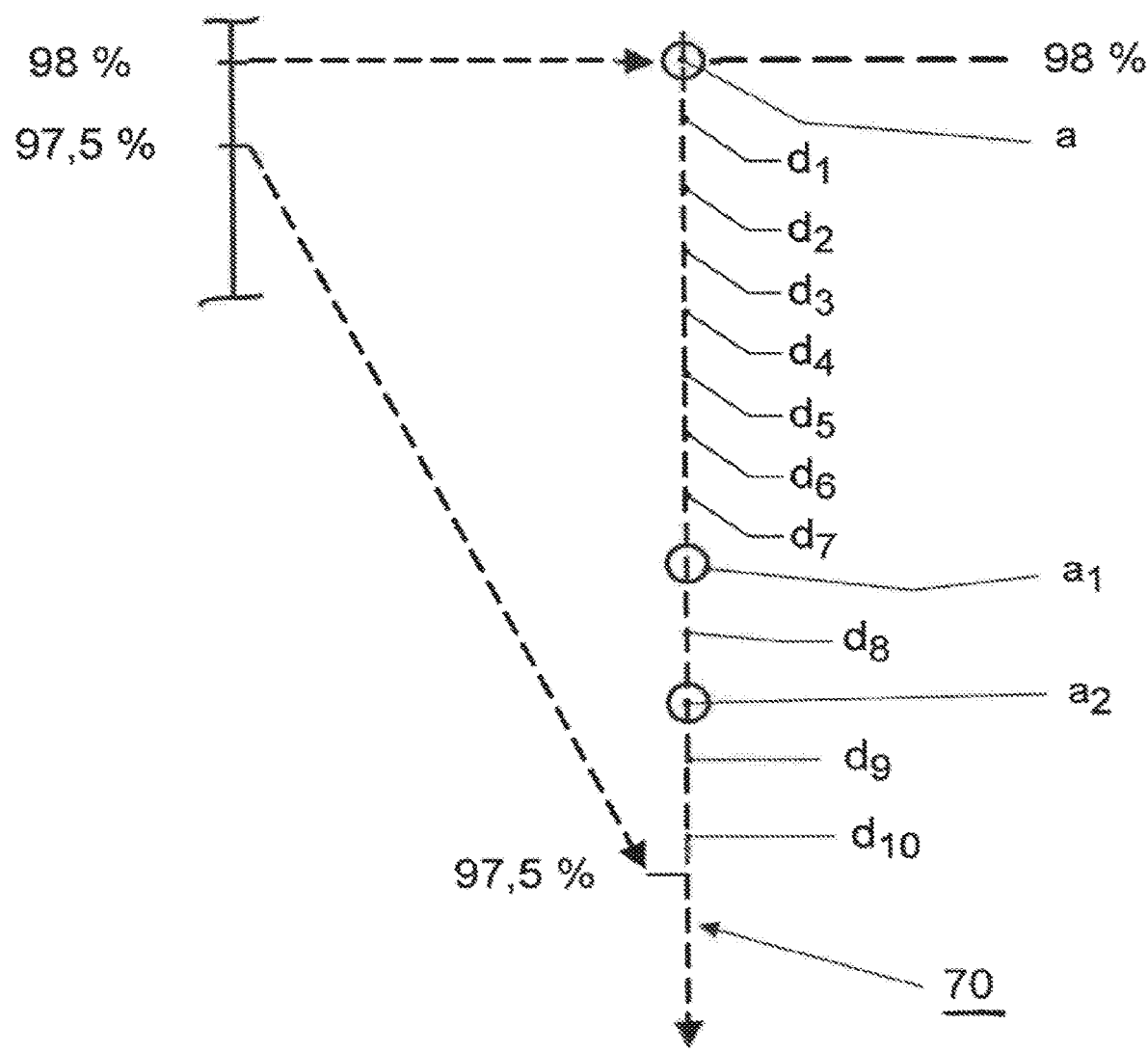
FIG. 15a illustrates a system diagram of a portion of a vertically oriented straight axis 70 between values 97.5% and 98% wherein, in addition to the pre-calculated solutions a, $a_1$, $a_2$ stored in the database, further solutions $d_1$, $d_2$ ... $d_{10}$ are added to the straight axis 70 as additional interpolation values by post-calculation in the sense of a "recombination".

The illustration of FIG. 15a symbolically shows a small portion of a straight, vertically oriented axis 70.

On the left side of the Figure, an original region is shown which is assumed to be located in a control region 76a according to FIG. 15, but is illustrated in a state cut off at the top and bottom. This region, which is located within a control region, is illustrated greatly magnified in the vertical direction in the right field of FIG. 15a. "Fixed interpolation points" from the pre-calculated stored solutions are provided, which are called a, $a_1$ and $a_2$. These fixed interpolation points are points of intersection of equivalent dose/volume graphs, corresponding to graph 60b of FIG. 15, but from three non-equal solutions. When a user navigates his point of intersection (the selector) 61b upwards or downwards within the control region 76a, he is able to reach point of intersection a, point of intersection $a_1$ and point of intersection $a_2$. At these points, there is a solution or a corresponding dose/volume graph having its point of intersection with the straight axis 70 here (as a criterion).

Effectively, the user displaces his selector (or the point of intersection which is here assumed to be located in "a") downwards towards $a_1$ or $a_2$. Within the system S of FIG. 1, actually new solutions are displayed, only one of these in each case.

When greater continuity is to be suggested to the user, i.e. when his movement starting from point a in a downward direction is to permit also smaller moves, intermediate solutions are calculated. Each one of the intermediate solutions has a point of intersection with the straight axis 70, which are illustrated by $d_1$, $d_2$ . . . $d_{10}$. These intermediate values are between two or even more already existing solutions and are generated by the calculation module 12 having access to the solutions stored in the database 10. These intermediate solutions are supplied via line 13a to the visualization module 11 which is capable of displaying the same via line 11a depending on the position, in which the user places the 'selector' on the straight portion 70 of FIG. 15a.

Only one solution is displayed in the DVH diagram 30 at a time in each case. When the user "displaces" his selector downwards, a next solution is displayed taking the place of the previous displayed solution on the dose/volume histogram 30.

It is apparent that the distances between the pre-calculated solutions decrease considerably and an extent of continuity is achieved which gives the user the feeling that he is displacing a graph in the dose/volume histogram. However, the perceived displacement itself is only an optical effect conveyed to the user, he rather selects a new graph in each case which in parallel causes a change to the other displayed dose/volume graphs so that all in all a new plan is displayed.

From a limited number of pre-calculated solutions, a great number of solutions arise due to the mentioned recombination in the calculation unit 12 so that the points of intersection thereof on the axis, which can be selected, form a virtually continuous control region, as shown in FIG. 15a including ten interpolation points and three pre-calculated values within a portion of 0.5 percent by volume.

Figure 15B:
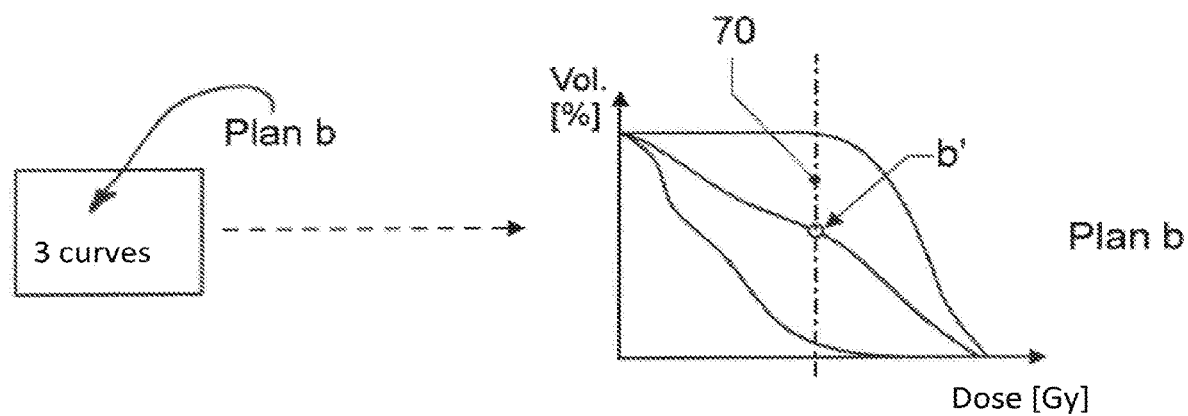

The following FIGS. 15b, 15c and 15d show the generation of these interpolation points by means of calculative recombination.

In FIG. 15b, only one solution is shown, which includes three graphs in the DVH diagram 30 in the—simplified—example, wherein the central graph intersects the vertical straight axis 70 and defines the point of intersection b'. Navigation is to be performed starting from this point of intersection, and there is a control region (as a navigation window) around this point of intersection which is determined by three pre-calculated plans in FIG. 15c. This navigation or control region 70a has three points of intersection, the upper limit, the lower limit and the point of intersection b' corresponding to plan b. Admittedly, the other two graphs also have points of intersection in FIG. 15b, however, they are not considered here.

Graphs corresponding to each other and present in the database 10 as pre-calculated solutions are combined in the control region 70a.

If no intermediate calculation was employed, i.e. no recombination, only three selectable points would be available to the user in the control region 70a. Normally, a much greater number of plans are available in a pre-calculated state so that a quasi-continuum is already present, however, this quasi-continuum can be further refined by the fact that a plurality of interpolation points is calculated by module 12 in accordance with the illustration of FIG. 15a, as symbolized by FIG. 15d.

When carefully examining the quasi-continuous region, it can be seen from FIG. 15d that it is composed of a plurality of individual points. When the user or planner navigates with his selector, i.e. when he "displaces" this selector on the straight axis 70, he gets the feeling that the transition from one displayed solution to the next displayed one is continuous. He will no longer feel the hops from one plan to the next, since the plans are so close to each other.

The intermediate plans calculated from stored plans a, b and c fill, for example, the singled-out region 70a' below plan b, which is a partial portion of the control region 70a described above in FIG. 15c. The module 12 of FIG. 1 introduces a plurality of intermediate plans into this region 70a', which intermediate plans are located below plan b and create a perceived continuum which is instinctively felt by the user during navigation.

Such a recombination can be calculated according to the following pattern.

In certain cases of conformity of the setting parameters, e.g. angular positions and energy values in the technical parameters of a plan, existing pre-calculated plans can be "recombined" permitting a transition from the originally discrete variety of such plans to a "continuous variety". When vectors $x_1, x_2 \ldots x_N$ denote the entirety of non-negative irradiation times for the re-combinable plans indicated by 1 to N, then said plans can be recombined via the weighted sum . . . .

$$X_{comb} = W_1 \cdot X_1 + W_2 \cdot X_2 + \ldots + W_N \cdot X_N$$

using the coefficients $w_1, w_2 \ldots w_N$ to form an entirety $X_{comb}$ and assuming non-negative irradiation times of a new plan.

If the variety of plans disintegrates into a plurality of subsets of plans which can each be recombined with each other, recombination is implemented within these subsets in each case.

Figure 16:
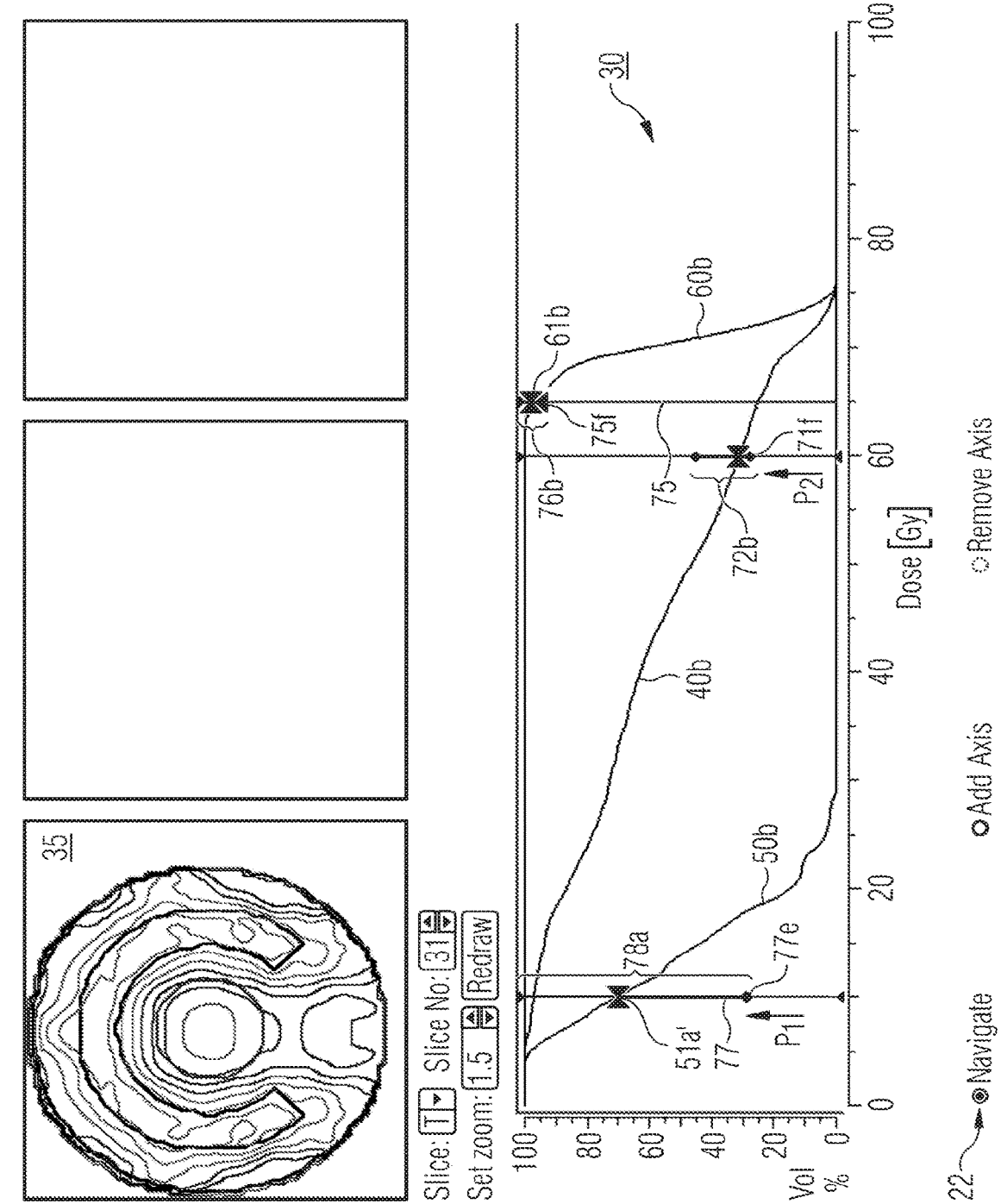
FIG. 16 shows a Figure following FIG. 15, wherein the lower limit value (lower restrictor 75f) is changed in an upward direction on the straight axis 75 associated with the tumor. The control interval 76a is again reduced and now has a length 76b only.

FIG. 16 stabilizes the high dose achieved according to FIG. 15 on the graph 60b for the tumor. When a value of 98% is achieved, this dose is not supposed to again deteriorate considerably during further navigation. Therefore, the lower restrictor, so far 75d in FIGS. 13/14, is raised and placed in a new position of approx. 97% just below the displaced starting point 61b. This placement causes an update of all control regions 72b, 78a. On graph 60b for the tumor (target), the new reduced control region 76b is present, which is determined by the upwards displaced lower restrictor 75f. Thus, the point of intersection 61b in the control region 76b cannot deteriorate further downwards.

Due to the narrow specification of the control region 76b on the risk graph 60b, a respective new control region 72b and 78a remains for the other two straight axes 71, 75, the lower limit values of which are 71f and 77e, respectively. For the risk, the lower value is raised to 31% instead of the original 3% of FIG. 14, and for the residual tissue on graph 40b, the lower value is raised to 31% instead of the previous 26% of FIG. 14. Arrows P1, P2 indicate the direction of change.

Figure 17:
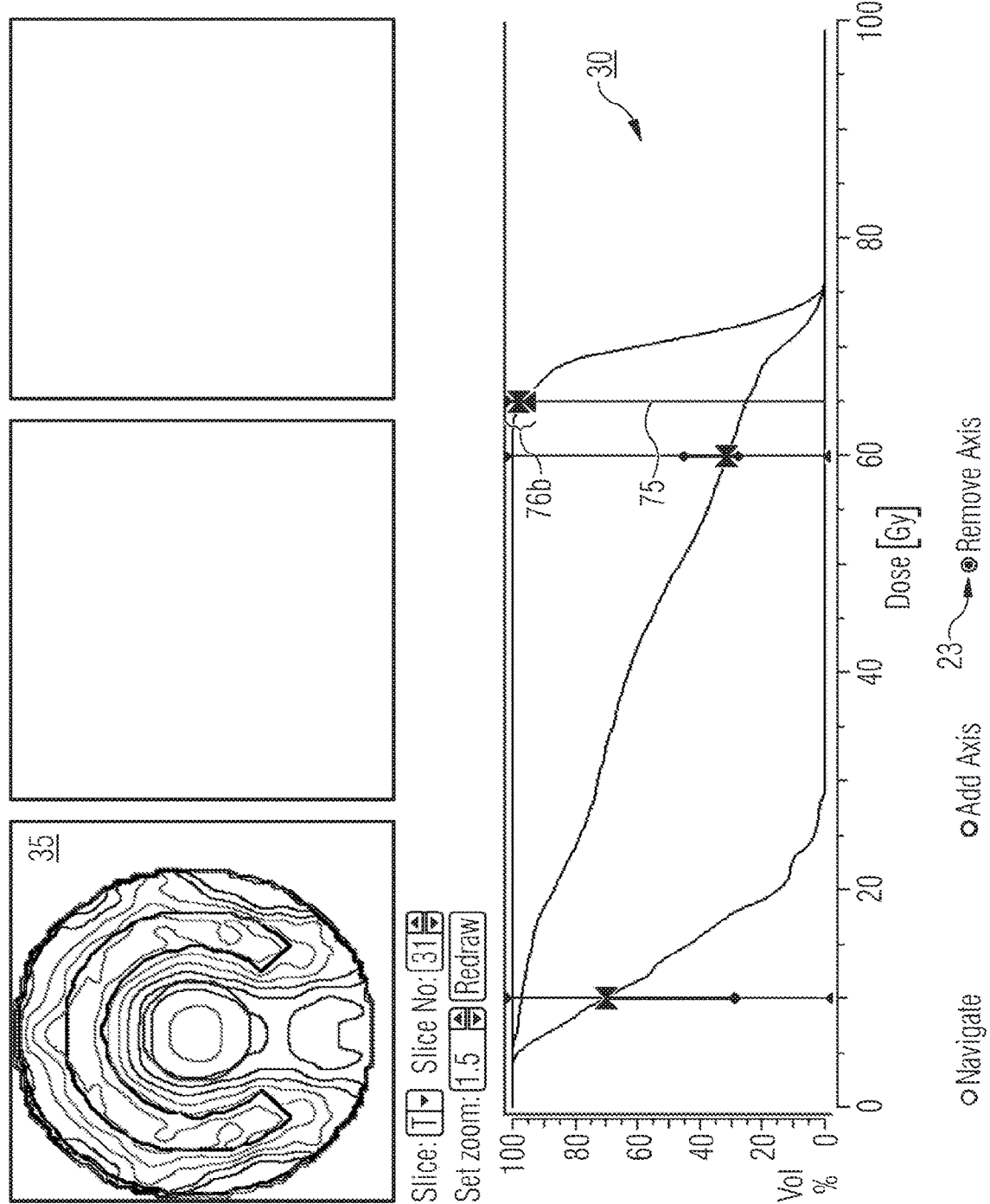
FIG. 17 is an illustration of a starting point for removing an axis (mode 'remove'). The mode is set to such an axis removal by button 23. The axis to be removed is axis 75.

FIG. 17 illustrates the starting point for removing a previously determined vertical axis. It is the tumor 75 axis which is to be removed. The mode selector 23 is activated and the axis 75 is removed by clicking thereon, as shown in FIG. 18.

Removal of the straight axis 75 also has an effect on the further navigation in that the restriction in the narrow control region 76b is eliminated, i.e. more solutions are enabled for the other control regions 72b and 78a. Thus, new control regions on the still present axes 71 and 77 arise as a result, which again have the original sizes 72 on the straight axis 71 and 78 on the straight axis 77.

Figure 18:
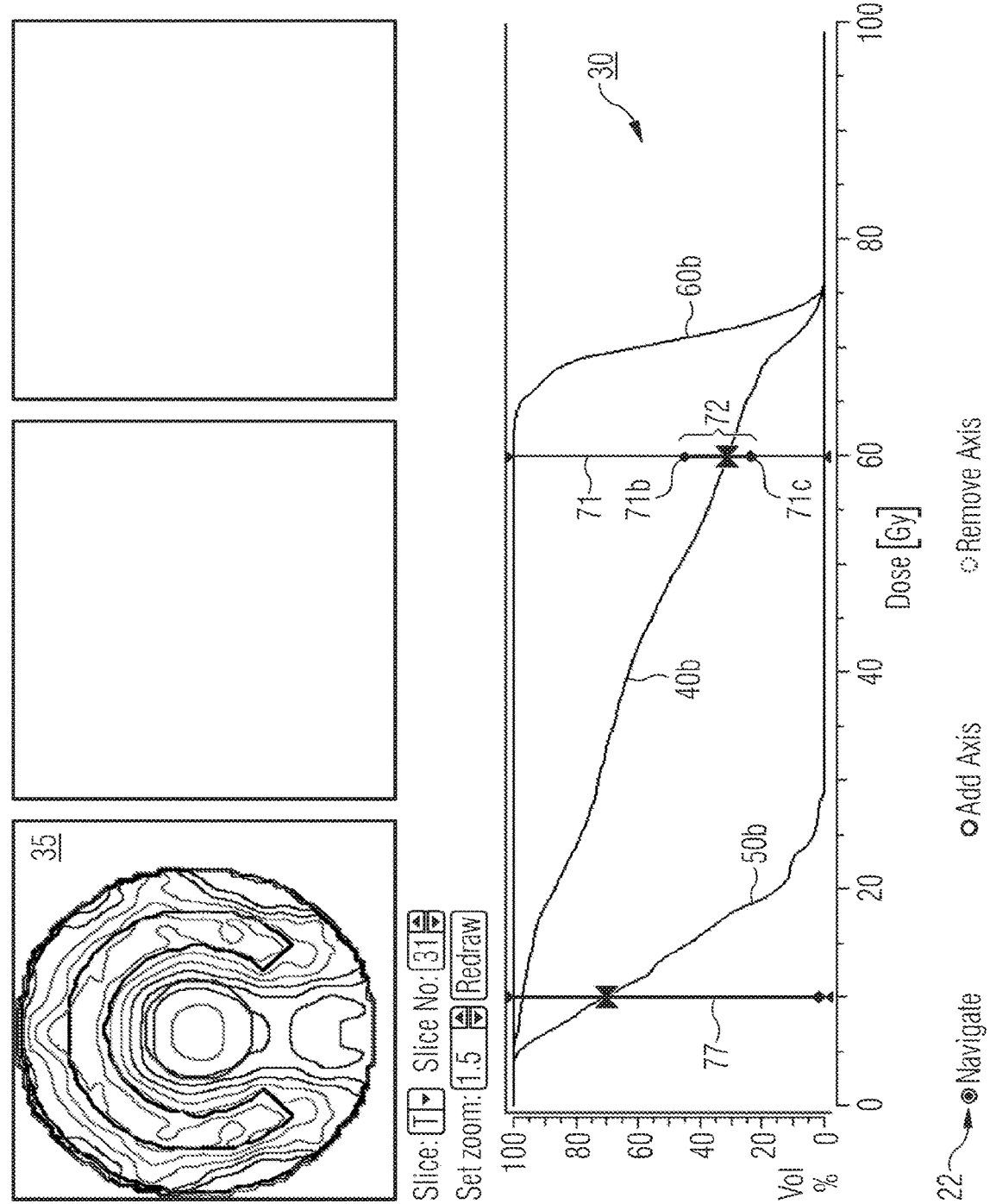
FIG. 18 illustrates FIG. 17 with the straight axis 75 removed, wherein the restrictions determined by it due to the narrow control region 76b also cease to apply.

After removing the vertical straight axis 75 (as a "criterion" for the target), FIG. 18 is obtained. The second solution including graphs 40b, 50b and 60b is still indicated therein. By selecting the mode (button 21 to "navigation"), navigation can be continued in FIG. 18 in accordance with the described types of restriction of the control regions or placement of vertical straight axes as a determination of criteria or "displacement" of the points of intersection.

Figure 19:
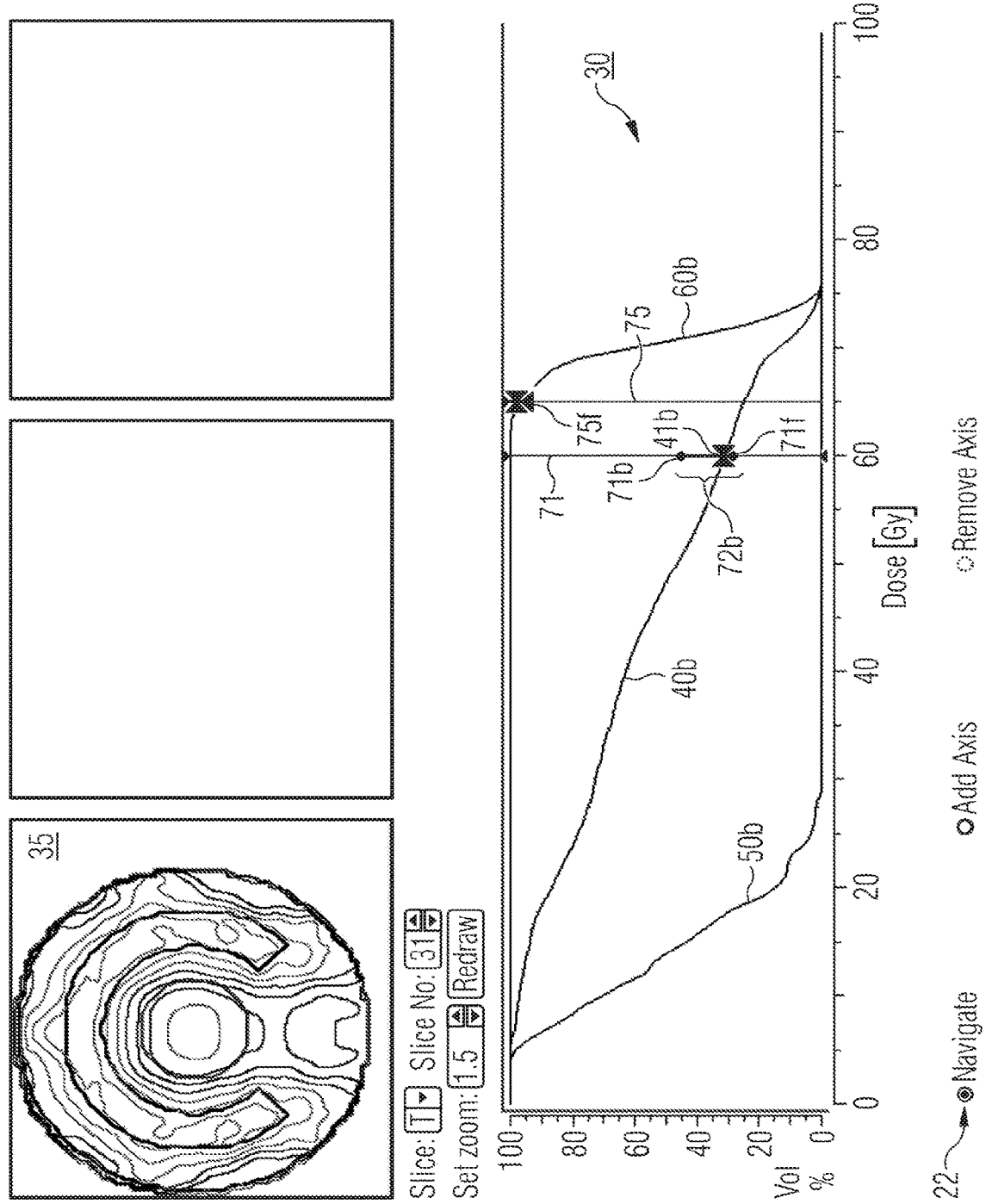
FIG. 19 shows the beginning of a further possible navigation step, i.e. the "extension". The control region 72b is to be expanded to a region below the lower end 71f of this control region 72b.

FIG. 19 shows the beginning of an extension. Extension is a change of a control region into a portion on the straight axis not yet occupied with pre-calculated solutions.

Extension is to be explained with reference to FIGS. 19, 20, 21 and 22.

The starting point is FIG. 19, which basically corresponds to FIG. 16 not including the third straight axis 77 inserted therein. The second and the first inserted straight axes 75 and 71 are shown and the point of intersection 41*b* on the straight axis 71 is located such that it is placed close to the lower end of the control region 72*b*. This point of intersection (selector) is to be displaced downwards ("selection" of new solutions). This is the starting point in FIG. 19, therefore the mode "navigation" (=nav) is activated by means of button 22.

A downward movement of the point of intersection 41*b* is hardly possible any longer on the DVH graph 40*b* in diagram 30, at best the lower final value 71*f* of the control region 72*b* can be selected and a corresponding solution can be displayed instead of the displayed solution 40*b*, 50*b*, 60*b*. This is all the range the user or planner is given.

Extension provides help here and enables a downward displacement of the lower limit 71*f*. The lower limit 71*f* is supposed to expand the control region downwards, where no pre-calculated plans have existed so far in the database 10 which can be displayed via the visualization module 11 on the display device 20 in the area of the DVH diagram 30.

From a scientific point of view, the result is as follows. The lower restriction in the tumor criterion (axis 77, restrictor 75*f* in FIG. 16) had the effect that the value range in the criterion of the residual body tissue (DVH graph 40*b*) ends just below the current selector position, i.e. a selection for improvement in this criterion would not be possible. When changing over to the next image, the lower extender is thus displaced downwards from 31% (of the percent-by-volume axis) in order to increase the value range in this direction.

Figure 20:
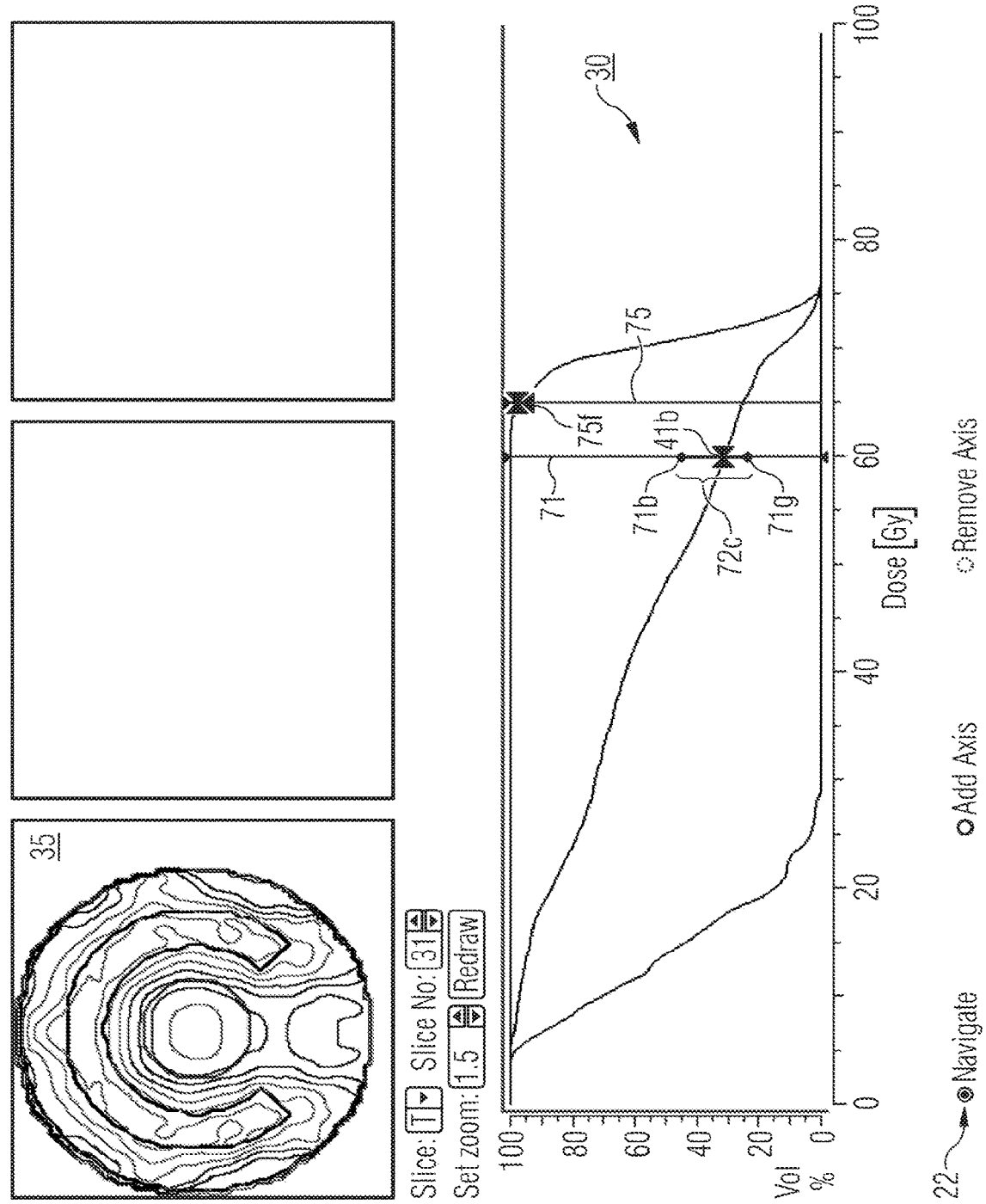
FIG. 20 illustrates the extension of the control region 72b to a not yet continuous greater length 72c (still open between 41b and 71g).

In practical application, the user/planner is provided with an expanded navigation region, his control region 72*c* is increased in FIG. 20, namely by the line portion between 41*b* and 71*g*.

Initially, this displacement of the lower limit 71*g* from 71*f* of FIG. 19 is a request and a signalization in the sense of a control (from a tablet screen or by means of a mouse pointer) transferred via the bidirectional connection 11*a* is to the visualization module 11, which causes a recalculation via the calculation module 12 for generating new plans and storing them in the database 10.

However, the line portion between 41*b* and 71*g* is initially empty and cannot be activated by a change or displacement of the point of intersection 41*b* on axis 71.

After completion of the calculations by the calculation module 12, intermediate plans are present, the control parameters of which for the technical device are configured such that they fill the gap between 41*b* and 71*g* (as a plurality of possible points of intersection) and form a complete graph of the DVH diagram 30 also in the residual region.

The addition of the new intermediate plans to the existing pre-calculated stock plans causes an update of the available value ranges (the control regions). A corresponding re-positioning of the 'extenders' in all criteria (the straight-line axes, i.e. axes 71 and 75 in the example of FIG. 20) is implemented, if necessary.

One example of how the numerical calculation can be implemented in the calculation module 12 can be found in Philipp Süss, A primal-dual barrier algorithm for the IMRT planning problem—An application to optimization-driven adaptive discretization, thesis, Department of Mathematics, TU Kaiserlautern, mensch and buch verlag, Berlin, Germany (2008).

The optimization process described therein is implemented such that the resulting criteria values for the viewed criterion are located between the previous end of the available value range and the desired criteria value, and are located within the axis portions limited by the respective restrictors for all other criteria.

In FIG. 20, the lower end of the control region 72*c* is changed and now amounts to 25% of the percent-by-volume axis only. The illustration of FIG. 21 arises as a result having a control region 72*c* occupied with points of intersection, wherein also the lower portion 72*b*' above the lower new end 71*g* is available including selectable values for a downward change of the point of intersection 41*b*.

The density of the post-calculated solutions, which are also placed in the database 10, can be made conditional on the size or length of the portion 72*b*' to be filled relative to the starting portion 72*b*.

Figure 21:
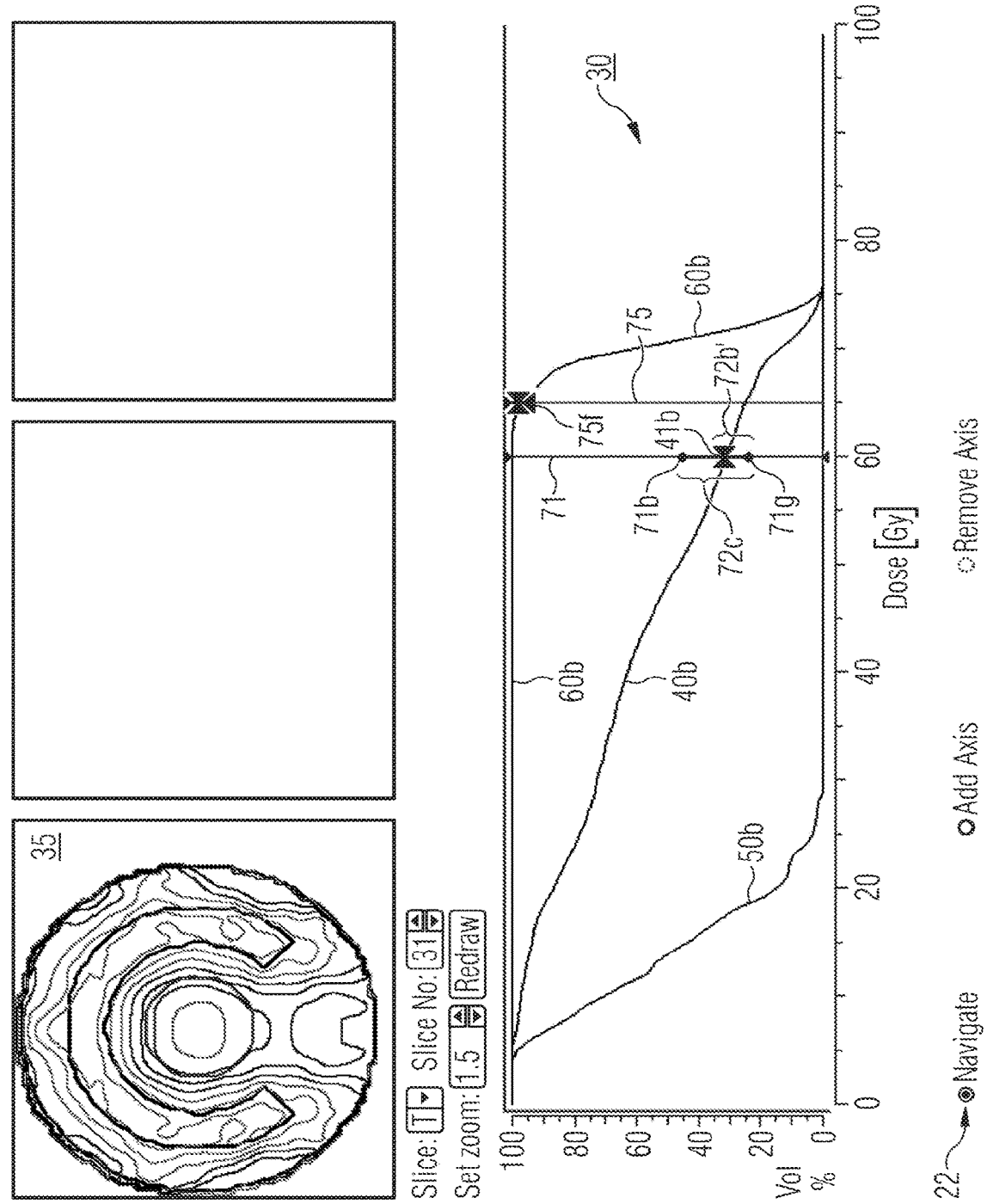
FIG. 21 illustrates the added portion 72b' which can now be used for changing the point of intersection 41b since this point of intersection 41b, as a "selector", can be changed in a downward direction, thereby displaying other solutions which, however, suggest to a user that they are achieved by displacement.
Figure 22:
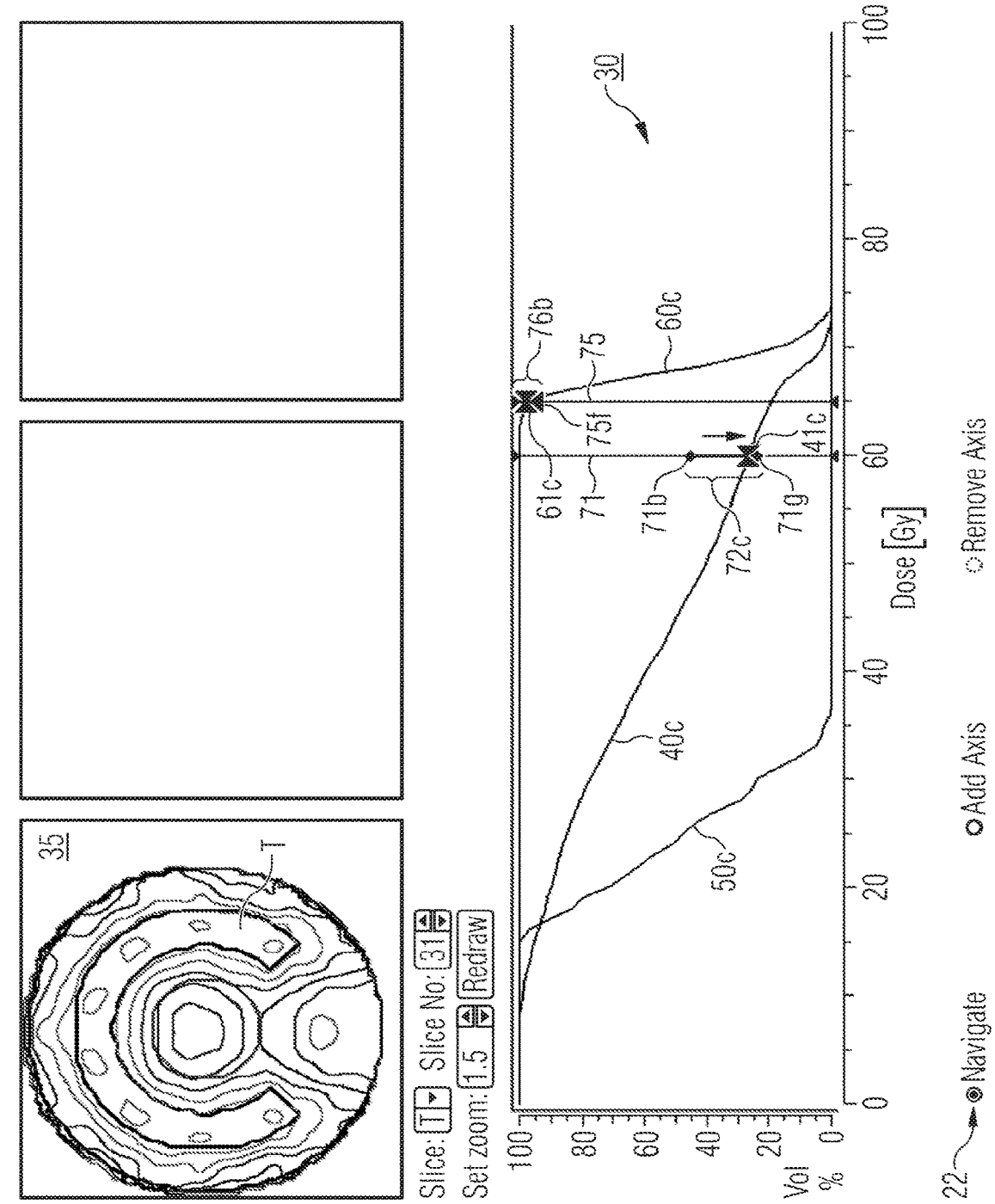
FIG. 22 shows a re-calculated third solution including the displayed/represented graphs 40c, 50c and 60c, which is achieved and displayed by a downward change of point 41b to point 41c, instead of the previously displayed solution of FIG. 21 including graphs 40b, 50b and 60b. The new graphs 40c, 50c and 60c represent a new solution achieved by recombination, wherein the point of intersection 41c is located on the straight axis.

This has happened in the following illustration of FIG. 22, preparations for which were made in FIGS. 19 to 21. The calculation module 12 has filled the region 72*b*' with values and the selector (or point of intersection 41*b*) on the straight axis 71 (the criterion) has been displaced downwards, as symbolized by the small downward arrow in FIG. 22, wherein a new point of intersection 41*c* selects one of the re-calculated graphs. This graph 40*c* is associated with a re-calculated third solution being represented, wherein the remaining associated graphs, here graphs 60*c* and 50*c* in the DVH diagram 30, are also updated with this graph. By updating the other graphs, auxiliary view 35 showing the isodoses is updated as well.

It is also ensured that the re-calculated graph 60*c* for the tumor volume T is within the specified control portion 76*b*, but extends considerably steeper in the descending branch. Point of intersection 61*c* with axis 75 of the control region 76*b* (with lower restriction 75*f*) can be displaced, however, remains within the specified control region 76*b*.

Evaluated as to quality, the central graph has been "displaced" downwards at higher dose values, in fact other plans have been displayed due to the downward displacement of point 41*b* to point 41*c*, which plans have lower percentages by volume at higher dose values, however, graph 50*c* for the risk is increased in dose value and its descending branch does not end at approx. 28 Gy, but at approx. 37 Gy.

What is claimed is:

1. A system as a planning tool for interactively selecting solutions during an interactive navigation of a user, the system comprising:
    a display device (20) for displaying graphs of dose/volume histograms (30) for the interactive navigation, wherein each dose/volume histogram has a number of dose/volume histogram curves;
    a visualization module (11) operating for buffering solutions read out from a database (10) via a data path (15), wherein the solutions are processed such that they are provided to the display device as a screen signal, and the screen signal yields a representation on the display device;
    wherein the visualization module is configured to:
        display a first dose/volume histogram as a main diagram, wherein one of a plurality of pre-calculated stored solutions from the database is visually represented at a time for manually selecting a first starting point (41*a*) on one, thereby selecting a curve (40*a*) of the number of dose/volume histogram curves and displaying a first straight axis (71,73) extending through the first starting point (41*a*);
        optically highlight a first region (72,74), located around the first starting point (41*a*) and on the first straight axis (71, 73), as a first straight portion having an upper and a lower limit to visualize, by a length extension between the limits, un-displayed solutions as stored and present in the database, but un-displayed by shapes of the curves, wherein the length of the first straight portion is defined by all points of intersections of the dose/volume histogram curves corresponding to the selected dose/volume histogram curve (40*a*).

2. The system according to claim 1, wherein the first straight portion having the upper and the lower limit and the length extension between the limits and the system allows the user to navigate within the length extension between the limits by moving the first starting point and display another dose/volume histogram curve.

3. The system according to claim 1, wherein a control element (71*e*) is provided that, by displacement thereof, restricts the first straight portion (76), from the top or bottom, to a reduced longitudinal extension (76*a*).

4. The system according to claim 1, wherein the visualization module (11) is configured to request a new plan, when a requested plan is not present in the database, and the new plan is generated by a calculation module (12) using pre-calculated plans stored in the database and read out via an access line (14).

5. The system according to claim 1, wherein a further starting point (61*a*) is manually selected by the user on another one of the number of dose/volume histogram curves; and wherein the visualization module is configured to:

receive a selection of a further starting point on the other dose/volume histogram curve and displaying a further straight portion (71,73) extending through the further starting point;

optically highlight a region (72,74), located around the further starting point and on the further straight portion, having an upper and a lower limit to visualize, by a length extension between the limits, un-displayed solutions as stored and present in the database, but un-displayed by shapes of the curves.

* * * * *